(12) United States Patent
Hoffman et al.

(10) Patent No.: US 8,715,664 B2
(45) Date of Patent: May 6, 2014

(54) USE OF HUMAN TNFα ANTIBODIES FOR TREATMENT OF EROSIVE POLYARTHRITIS

(75) Inventors: Rebecca S. Hoffman, Wilmette, IL (US); Mark Weinberg, Wilmette, IL (US)

(73) Assignee: AbbVie Biotechnology Ltd., Hamilton (BM)

( * ) Notice: Subject to any disclaimer, the term of this patent is extended or adjusted under 35 U.S.C. 154(b) by 434 days.

(21) Appl. No.: 11/435,844

(22) Filed: May 16, 2006

(65) Prior Publication Data

US 2007/0071747 A1    Mar. 29, 2007

Related U.S. Application Data

(60) Provisional application No. 60/681,645, filed on May 16, 2005.

(51) Int. Cl.
*A61K 39/395* (2006.01)
*C07K 16/24* (2006.01)

(52) U.S. Cl.
USPC ............... 424/142.1; 424/145.1; 530/388.15; 530/388.23

(58) Field of Classification Search
None
See application file for complete search history.

(56) References Cited

U.S. PATENT DOCUMENTS

| | | |
|---|---|---|
| 5,231,024 A | 7/1993 | Moeller et al. |
| 5,654,407 A | 8/1997 | Boyle et al. |
| 5,656,272 A | 8/1997 | Le et al. |
| 5,705,389 A | 1/1998 | Braham et al. |
| 5,795,967 A | 8/1998 | Aggarwal et al. |
| 5,859,205 A | 1/1999 | Adair et al. |
| 5,877,293 A | 3/1999 | Adair et al. |
| 5,888,511 A | 3/1999 | Skurkovich et al. |
| 5,929,212 A | 7/1999 | Jolliffe et al. |
| 5,994,510 A | 11/1999 | Adair et al. |
| 6,090,382 A | 7/2000 | Salfeld et al. |
| 6,214,870 B1 | 4/2001 | McClure et al. |
| 6,235,281 B1 | 5/2001 | Stenzel et al. |
| 6,258,562 B1 | 7/2001 | Salfeld et al. |
| 6,270,766 B1 | 8/2001 | Feldman et al. |
| 6,372,715 B1 | 4/2002 | Kaltwasser et al. |
| 6,379,666 B1 | 4/2002 | Tobinick |
| 6,419,944 B2 | 7/2002 | Tobinick |
| 6,423,321 B2 | 7/2002 | Tobinick |
| 6,448,380 B2 | 9/2002 | Rathjen et al. |
| 6,451,983 B2 | 9/2002 | Rathjen et al. |
| 6,498,237 B2 | 12/2002 | Rathjen et al. |
| 6,509,015 B1 * | 1/2003 | Salfeld et al. |
| 6,593,458 B1 | 7/2003 | Rathjen et al. |
| 7,012,135 B2 | 3/2006 | Athwal et al. |
| 7,070,775 B2 | 7/2006 | Le et al. |
| 7,153,507 B2 | 12/2006 | Van De Winkel et al. |
| 7,192,584 B2 | 3/2007 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,541,031 B2 | 6/2009 | Salfeld et al. |
| 7,588,761 B2 | 9/2009 | Salfeld et al. |
| 7,863,426 B2 | 1/2011 | Wan et al. |
| 2001/0004456 A1 | 6/2001 | Tobinick |
| 2001/0016195 A1 | 8/2001 | Tobinick |
| 2001/0021380 A1 | 9/2001 | Pluenneke |
| 2001/0026801 A1 | 10/2001 | Tobinick |
| 2003/0012786 A1 | 1/2003 | Teoh et al. |
| 2003/0049725 A1 | 3/2003 | Heavner et al. |
| 2003/0161828 A1 | 8/2003 | Abdelghany et al. |
| 2003/0206898 A1 | 11/2003 | Fischkoff et al. |
| 2003/0219438 A1 | 11/2003 | Salfeld et al. |
| 2003/0235585 A1 * | 12/2003 | Fischkoff et al. |
| 2004/0009166 A1 | 1/2004 | Filpula et al. |
| 2004/0009172 A1 | 1/2004 | Fischkoff et al. |
| 2004/0033228 A1 | 2/2004 | Krause et al. |
| 2004/0120952 A1 | 6/2004 | Knight et al. |
| 2004/0126372 A1 * | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0166111 A1 | 8/2004 | Kaymakcalan et al. |
| 2004/0170626 A1 | 9/2004 | Schuurman et al. |

(Continued)

FOREIGN PATENT DOCUMENTS

| | | |
|---|---|---|
| EP | 0101681 B1 | 3/1984 |
| EP | 0186833 B1 | 7/1986 |

(Continued)

OTHER PUBLICATIONS

Ogilvie et al. British Journal of Dermatology, 144(3):587-589, Mar. 2001.*
Fundamental Immunology, William E. Paul, M.D. ed., 3rd ed., p. 242, 292-295, 1993.*
Rudikoff et al. Proc. Natl. Acad. Sci. USA, 79(6):1979-1983, Mar. 1982.*
MacCallum et al. J. Mol. Biol., 262, 732-745, 1996.*
Casset et al. Biochemical and Biophysical Research Communications, 307:198-205, 2003.*

(Continued)

*Primary Examiner* — Ilia Ouspenski

(74) *Attorney, Agent, or Firm* — Foley Hoag LLP

(57) ABSTRACT

The invention describes methods of treating erosive polyarthritis comprising administering a TNFα antibody, or antigen-binding portion thereof. The invention also describes a method for testing the efficacy of a TNFα antibody, or antigen-binding portion thereof, for the treatment of erosive polyarthritis.

33 Claims, 5 Drawing Sheets

(56) References Cited

U.S. PATENT DOCUMENTS

| | | |
|---|---|---|
| 2004/0219142 A1 | 11/2004 | Banerjee et al. |
| 2005/0123541 A1 | 6/2005 | Heavner et al. |
| 2005/0249735 A1 | 11/2005 | Le et al. |
| 2005/0255532 A1 | 11/2005 | Ruben et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0153846 A1 | 7/2006 | Krause et al. |
| 2006/0246073 A1 | 11/2006 | Knight et al. |
| 2007/0003548 A1 | 1/2007 | Heavner et al. |
| 2007/0041905 A1 | 2/2007 | Hoffman et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0196373 A1 | 8/2007 | Le et al. |
| 2007/0202104 A1 | 8/2007 | Banerjee et al. |
| 2007/0249813 A1 | 10/2007 | Salfeld et al. |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2008/0227136 A1 | 9/2008 | Pla et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0110679 A1 | 4/2009 | Li et al. |
| 2009/0123378 A1 | 5/2009 | Wong et al. |
| 2009/0148513 A1 | 6/2009 | Fraunhofer et al. |
| 2009/0155205 A1 | 6/2009 | Salfeld et al. |
| 2009/0226530 A1 | 9/2009 | Lassner et al. |
| 2009/0239259 A1 | 9/2009 | Hsieh et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong et al. |
| 2010/0034823 A1 | 2/2010 | Borhani et al. |
| 2010/0040604 A1 | 2/2010 | Salfeld et al. |
| 2010/0160894 A1 | 6/2010 | Julian et al. |
| 2010/0278822 A1 | 11/2010 | Fraunhofer et al. |
| 2011/0054414 A1 | 3/2011 | Shang et al. |

FOREIGN PATENT DOCUMENTS

| | | | |
|---|---|---|---|
| EP | | 0212489 B1 | 3/1987 |
| EP | | 0351789 B1 | 1/1990 |
| EP | | 0366043 B1 | 5/1990 |
| EP | | 0492448 B1 | 7/1992 |
| EP | | 0614984 B1 | 9/1994 |
| EP | | 0659766 A1 | 6/1995 |
| GB | | 2279077 | 12/1994 |
| WO | WO-91/02078 A1 | | 2/1991 |
| WO | WO-92/11383 A1 | | 7/1992 |
| WO | WO-92/16553 A1 | | 10/1992 |
| WO | WO-93/06213 A1 | | 4/1993 |
| WO | WO-93/11793 A1 | | 6/1993 |
| WO | WO-94/29347 A1 | | 12/1994 |
| WO | WO-95/23813 A1 | | 9/1995 |
| WO | WO 9729131 A1 * | | 8/1997 |
| WO | WO-98/05357 A1 | | 2/1998 |
| WO | WO-01/00229 A1 | | 1/2001 |
| WO | WO01/94585 | | 6/2001 |
| WO | WO 0212502 A2 * | | 2/2002 |
| WO | WO-02/100330 A3 | | 12/2002 |
| WO | WO03/016468 | | 2/2003 |
| WO | WO 2004/009776 A2 | | 1/2004 |
| WO | WO-2006/041970 A2 | | 4/2006 |

OTHER PUBLICATIONS

Zhou et al. J. Clin. Pharmacol., 47:383-396, 2007.*
Queiro-Silva et al. Ann. Rheum. Dis. 62:68-70, 2003.*
Clinical Trial NCT00646386 (2003, clinicaltrials.gov/show/NCT00646386, accessed on Aug. 1, 2013), 3 pages.*
Mazumdar et al., "Golimumab." mAbs (2009), 1: 442-431.*
Abraham, Edward, et al., "Efficacy and Safety of Monoclonal Antibody to Human Tumor Necrosis Factor α in Patients with Sepsis Syndrome," *JAMA*, vol. 273(12):934-941 (1995).
Asli, Bouchra et al., "Inhibition of Tumor Necrosis Factor a and Ankylosing Spondylitis," *N. Engl. J. Med.*, vol. 348(4):359-361 (2003).
Awni, Walid M. et al., "Steady-State Pharmacokinetics (PK) of Adalimumab (HUMIRA™,Abbott) Following 40 mg Subcutaneous (sc) Injection Every Other Week (eow) in Rheumatoid Arthritis (RA) Patients with and without Methotrexate (MTX) Background Therapy," *Arthritis Rheum.*, vol. 48(Suppl. 9):S140 (2003).
Bansback, Nick J. et al., "The Cost Effectiveness of Adalimumab (HUMIRA™, Abbott) in the Treatment of Patients with Moderate to Severe Rheumatoid Arthritis (RA)," *Arthritis Rheum.*, vol. 48 (Suppl. 9):S611 (2003).
Barbuto, J.A.M. et al. "Production of Neutralizing Antibodies to Tumor Necrosis Factor by Human Tumor-Infiltrating B Lymphocytes" *Proc. Am. Assoc. Cancer Res,*. 34:487, Abstr. 2904 (1993).
Barrera, P. et al., "Drug survival, efficacy and toxicity of monotherapy with a fully human anti-tumour necrosis with a fully human anti-tumour necrosis factor-α antibody compared with methotrexate in long-standing rheumatoid arthritis," *Rheumatology*, vol. 41:430-439 (2002).
Barrera, Pilar et al., "Effect of a Fully Human Anti-TNFα Monoclonal Antibody on the Local and Systemic Expression of TNFα and IL-1β," *Arthritis Rheum.*, vol. 42(9 Suppl.):S75 (1999).
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Boeger, C.A. et al., "Treatment of ankylosing spondylitis with infliximab," *Ann. Rheum Dis.*, vol. 60(12):1159-1160 (2001).
Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).
Bombardier, C. et al., "Pattern of DMARD use in a North American Cohort of Patients with Early Rheumatoid Arthritis (RA) (SONORA)," *Arthritis Rheum.*, vol. 46(9 Suppl.):S344 (2002).
Boyle, P. et al. "A Novel Monoclonal Human IgM Autoantibody which Binds Recombinant Human and Mouse Tumor Necrosis Factor-" *Cell. Immunol.*, 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).
Brandt, Jan et al., "Successful Treatment of Active Ankylosing Spondylitis with the Anti-Tumor Necrosis Factor a Monoclonal Antibody Infliximab," *Arthritis & Rheumatism*, vol. 43(6):1346-1352 (2000).
Brandt, Jan et al., "Successful Short Term Treatment of Severe Undifferentiated Spondyloarthropathy with the Anti-Tumor Necrosis Factor-a Monoclonal Antibody Infliximab," *The Journal of Rheumatology*, vol. 29:118-122 (2002).
Braun, Juergen et al., "Therapy of ankylosing spondylitis and other spondyloarthritides: established medical treatment, anti-TNF-a therapy and other novel approaches," *Arthritis Res.*, vol. 4:307-321 (2002).

(56) References Cited

OTHER PUBLICATIONS

Braun, J. et al., "Anti-tumour necrosis factor a therapy for ankylosing spondylitis: international experience," *Ann. Rheum. Dis.*, vol. 61(Suppl. III):iii51-iii60 (2002).
Braun, J. et al., "Treatment of active ankylosing spondylitis with infliximab: a randomised controlled multicentre trial," *The Lancet*, vol. 359(9313):1187-1193 (2002).
Braun, Jüergen et al., "New Treatment options in spondyloarthropathies: increasing evidence for significant efficacy of anti-tumor necrosis factor therapy," *Curr. Opin. Rheumatol.*, vol. 13:245-249 (2001).
Braun, J. et al., "Anti-TNFa: a new dimension in the pharmacotherapy of the spondyloarthropathies!?," *Ann. Rheum. Dis.*, vol. 59(6):404-407 (2000).
Braun, J. et al., "International ASAS consensus statement for the use of anti-tumour necrosis factor agents in patients with ankylosing spondylitis," *Ann. Rheum. Dis.*, vol. 62:817-824 (2003).
Braun, Juergen et al., "Novel approaches in the treatment of ankylosing spondylitis and other spondyloarthritides," *Expert Opin. Investig. Drugs.*, vol. 12(7):1097-1109 (2003).
Braun, Juergen et al., "Biologic therapies in the spondyloarthritis: new opportunities, new challenges," *Current Opinion in Rheumatology*, vol. 13:394-407 (2003).
Breban, M. et al., "Efficacy of infliximab in refractory ankylosing spondylitis: results of a six-month open-label study," *Rheumatology*, vol. 41:1280-1285 (2002).
Breedveld, F.C. et al., "Sustained Efficacy Over 4 Years with Adalimumab in Patients with Active Rheumatoid Arthritis," *Ann. Rheum. Dis.*, vol. 62(Suppl. 1):169 (2003).
Breedveld, Ferdinand C. et al., "Sustained Efficacy over 5 Years with Adalimumab (HUMIRA™) in Patients with Active Rheumatoid Arthritis," *Arthritis Rheum.*, vol. 48(Suppl. 9):S118 (2003).
Breedveld, F. et al., "The Long-term Efficacy and Safety of Adalimumab (D2E7), the Fully Human Anti-TNF Monoclonal Antibody, in Combination with Methotrexate in the Treatment of Rheumatoid Arthritis: Results of a 2-Year Study," *JCR: Journal of Clinical Rheumatology*, vol. 8(Suppl. 3):546 (2002).
Breedveld, F.C. et al., "The Fully Human Anti-TNF Antibody Adalimumab (D2E7) in Combination with Methotrexate (MTX) in the Treatment of Active Rheumatoid Arthritis: Results of a 2-Year Study," Presented at: The Annual Meeting of the European League Against Rheumatism (EULAR), Prague, Czech Republic, Jun. 2001.
Brekke, Ole Henrik et al., "Therapeutic Antibodies for Human Diseases at the Dawn of the Twenty-first Century," *Nature*, vol. 2:52-62 (2002).
Burmester, G.R. et al., "Long-Term Efficacy and Safety of Adalimumab (D2E7) Monotherapy in Patients With DMARD-Refractory Rheumatoid Arthritis—Results From a 2-Year Study," *Arthritis Rheum.*, vol. 46(9 Suppl.):S537 (2002).
Burmester, G.R. et al., "Effect of Dose Interruptions on the Efficacy and Safety of Adalimumab in Patients with RA," *Ann. Rheum. Dis.*, vol. 62(Suppl. 1):192 (2003).
Burmester, G.R. et al., "Sustained Efficacy of Adalimumab Monotherapy for More than Four Years in DMARD-Refractory RA," *Ann. Rheum. Dis.*, vol. 62(Suppl. 1):192-3 (2003).
Case, John P., "Old and New Drugs Used in Rheumatoid Arthritis: A Historical Perspective," *American Journal of Therapeutics*, vol. 8:163-179 (2001).
Chartash, E.K. et al., "Adalimumab Improves Fatigue in Patients with Active Rheumatoid Arthritis," *Ann. Rheum. Dis.*, vol. 62(Suppl. 1):349 (2003).
Chow, A.W. et al. "Effect of monoclonal antibody on human tumor necrosis factor (TNF MAb) on TNFa, IL-1β, and IL-6 levels in patients with sepsis syndrome" *Clinical Research*, 42:2 299A (1994).
Cohen, Jonathan, et al., "Intercept: An international, multicenter, placebo-controlled trial of monoclonal anitbody to human tumor necrosis factor-α in patients with sepsis," *Crit Care Med*, vol. 24(9):1431-1440 (1996).
Cox, J.P.L. et al. "A directory of human germ-line $V_k$ segments reveals a strong bias in their usage" *Eur. J. Immunol.*, 24(2):827-36 (1994).

Dayer, Jean-Michel et al., "Anti-TNF-a Therapy for Ankylosing Spondylitis—A Specific or Nonspecific Threatment?" *N. Engl. J. Med.*, vol. 346(18):1399-1400 (2002).
den Broeder, A.A. et al, "The Effect of D2E7, a new human anti-TNFα monoclonal antibody, on the oxidative burst of PMN in patients with RA," *Arthritis and Rheumatism*, vol. 41(9):S57 (1998).
den Broeder, Alfons et al., "A Single Dose, Placebo Controlled Study of the Fully Human Anti-Tumor Necrosis Factor-α Antibody Adalimumab (D2E7) in Patients with Rheumatoid Arthritis," *The Journal of Rheumatology*, vol. 29(11):2288-2298 (2002).
den Broeder, A.A. et al., "Long term anti-tumour necrosis factor α monotherapy in rheumatoid arthritis: effect on radiological course and prognostic value of markers of cartilage turnover and endothelial activation," *Ann. Rheum. Dis.*, vol. 61:311-318 (2002).
Department of Surgery, University of Toronto, Annual Report (1998-1999).
Dernis, E. et al., "Infliximab in spondylarthropathy—Influence on bone density," *Clin. Exp. Rheumatol.*, vol. 20(Suppl. 28):S185-S186 (2002).
Egan, L.J. et al, "A randomized, single-blind, pharmacokinetic and doseresponse study of subcutaneous methotrexate, 15 and 25 MG/week, for refractory ulcerative colitis and Crohn's Disease," *Gastroenterology*, vol. 114(4):G3978 (1998).
Elliott, M.J. et al. "Treatment of rheumatoid arthritis with chimeric monoclonal antibodies to tumor necrosis factor a" *Arthritis & Rheumatism*, 36(12):1681-90 (1993).
Emery, Paul et al., "Changes in PRO-MMP-1 in Relation to Standard Measures of Disease Activity Over a 6 Month Treatment Period with Adalimumab (D2E7) in Rheumatoid Arthritis," *Arthritis & Rheumatism*, vol. 44(9):S215 (2001).
Emery, Paul et al., "Improvement in HAQ Disability in Rheumatoid Arthritis (RA) with Adalimumab (HUMIRA™) Based on Duration of Disease," *Arthritis Rheum.*, vol. 48(Suppl. 9):S313 (2003).
Feldmann, Marc et al., "Anti-TNFα Therapy of Rheumatoid Arthritis: What Have We Learned," *Annu. Rev. Immunol.*, vol. 19:163-196 (2001).
Figini, Mariangela et al., "In Vitro Assembly of Repertoires of Antibody Chains on the Surface of Phage by Renaturation," *J. Mol. Biol.*, vol. 239:68-78 (1994).
Fomsgaard, A. et al. "Auto-antibodies to Tumour Necrosis Factor a in Healthy Humans and Patients with Inflammatory Diseases and Gram-Negative Bacterial Infections" *Scand. J. Immunol.*, 30:219-23 (1989).
Foote, Jefferson et al., "Antibody Framework Residues Affecting the Conformation of the Hypervariable Loops," *J. Mol. Biol.*, vol. 224:487-499 (1992).
Furst, D.E. et al., "Safety and Efficacy of Adalimumab (D2E7), a Fully Human Anti-TNF-α Monoclonal Antibody, Given in Combination with Standard Antirheumatic Therapy: Safety Trial of Adalimumab in Rheumatoid Arthritis," *Arthritis Rheum.*, vol. 46(9 Suppl.):S572 (2002).
Furst, Daniel E. et al., "Adalimumab, a Fully Human Anti-Tumor Necrosis Factor-α Monoclonal Antibody, and Concomitant Standard Antirheumatic Therapy for the Treatment of Rheumatoid Arthritis: Results of STAR (Safety Trial of Adalimumab in Rheumatoid Arthritis)," *The Journal of Rheumatology*, vol. 30(12):2563-2571 (2003).
Furst, Daniel et al., "TNF Blockade by the Fully Human Monoclonal Antibody Adalimumab (D2E7), in the Armada Trial Results in Decreases in Serum Matrix Metalloproteinase (MMP) Levels Along with Impressive Clinical Improvement in Refractory RA Patients," *Arthritis Rheum.*, vol. 44(9 Suppl.):S215 (2001).
Furst, Daniel E. et al., "Improvement of the Individual ACR Components in ACR20 Responders in an Adalimumab (HUMIRA™) RA Clinical Trial," *Arthritis Rheum.*, vol. 48(Suppl. 9):S106 (2003).
Gorman, Jennifer D. et al., "Treatment of Ankylosing Spondylitis by Inhibition of Tumor Necrosis Factor a," *The New England Journal of Medicine*, vol. 346(18):1349-1356 (2002).
Goto, Daisuke et al., "Adalimumab," Medline AC NLM12510366 (2002).
Goto, Daisuke et al., "Adalimumab," *Nippon Rinsho*, 60(12): 2384-2389 (2002).
Granneman, Richard G. et al., "Pharmacokinetic/Pharmacodynamic (PK/PD) Relationships of Adalimumab (HUMIRA™, Abbott) in

(56) References Cited

OTHER PUBLICATIONS

Rheumatoid Arthritis (RA) Patients during Phase II/III Clinical Trials," *Arthritis. Rheum.*, vol. 48(Suppl. 9):S140 (2003).
Griffiths, A.D. et al. "Human anti-self antibodies with high specificity from phage display libraries" *The EMBO J.*, 12(2):725-34 (1993).
Hawkins, Robert E. et al., "Selection of Phage Antibodies by Binding Affinity Mimicking Affinity Maturation," *J. Mol. Biol.*, vol. 226:889-896 (1992).
Holler, E. et al., "Modulation of Acute Graft-Versus-Host Disease After Allogeneic Bone Marrow Transplantation by Tumor Necrosis Factor α (TNFα) Release in the Course of Pretransplant Conditioning: Role of Conditioning Regimens and Prophylactic Application of a Monoclonal Antibody Neutralizing Human TNFα (MAK 195F)," *Blood*, vol. 86(3):890-899 (1995).
Holliger, Philipp et al., "Engineered antibody fragments and the rise of single domains," *Nature Biotechnology*, vol. 23(9):1126-1136 (2005).
Hoogenboom, Hennie R. et al., "Converting rodent into human antibodies by guided selection," *Antibody Engineering*, Oxford University Press, Chpt. 8, pp. 169-185 (1996).
Horneff, G. et al., "TNF-a antagonists for the treatment of juvenile-onset spondyloarthritides," *Clin. Exp. Rheumatol.*, vol. 20(Suppl. 28):S137-S142 (2002).
Huse, W.D. et al. "Generation of a large combinatorial library of the immunoglobulin repertoire in phage lambda" *Science*, 246:1275-81 (1989).
Janeway, Charles A., Jr., "The structure of a typical antibody molecule," *Immunobiology*, vol. 5, Garland Publishing, pp. 94-105 (2001).
Janeway, Charles A., Jr., "The Protein Products of MHC class I and class II genes are highly polymorphic," Immunobiolgy, Third Edition, pp. 4:24-4:30 (1997).
Jespers, Laurent S. et al., "Guiding the Selection of Human Antibodies from Phage Display Repertoires to a Single Epitope of an Antigen," *Bio/Technology*, vol. 12:899-903 (1994).
Kaiser, M.J. et al., "Efficacy of infliximab (Remicade®) in the treatment of spondyloarthropathies. Two case reports," *Joint Bone Spine*, vol. 68:525-527 (2001).
Kanakoudi-Tsakalidou, F. et al., "Influenza vaccination in children with chronic rheumatic diseases and long-term immunosuppressive therapy," *Clinical and Experimental Rheumatology*, vol. 19:589-594 (2001).
Kavanaugh, A.F. et al., "The Armada Trial: 12-Month Efficacy and Safety of Combination Therapy with Adalimumab (D2E7), the First Fully Human Anti-TNF Monoclonal Antibody, and Methotrexate (MTX) in Patients with Active Rheumatoid Arthritis," *Ann. Rheum. Dis.*, vol. 61(Suppl. I):S168 (2002).
Kavanaugh, A. et al., "Immune Response is Not Affected by Adalimumab Therapy," *Ann. Rheum. Dis.*, vol. 62(Suppl. 1):169 (2003).
Kavanaugh, Arthur F. et al., "Treatment with Adalimumab (D2E7) does not Affect Normal Immune Responsiveness," *Arthritis Rheum.*, vol. 46(9 Suppl.):S132 (2002).
Kaymakcalan, Z. et al., "Comparison of Adalimumab (D2E7), Infliximab, and Etanercept in the Prevention of Polyarthritis in the Transgene Murine Model of Rheumatoid Arthritis," *Arthritis, Rheum.*, vol. 46(9 Suppl.):S304 (2002).
Kaymakcalan, Z. et al., "Murine Model for Assessing Adalimumab, Inflixmab, and Etanercept to Prevent Polyarthritis," *Ann. Rheum. Dis.*, vol. 62(Suppl. 1):136-7 (2003).
Kempeni, Joachim, "Update on D2E7: a fully human anti-tumour necrosis factor α monoclonal antibody," *Ann. Rheum. Dis.*, vol. 59(Suppl. 1):144-145 (2000).
Kempeni, Joachim, "Preliminary Results of early clinical trials with the fully human anti-TNFα monoclonal antibody D2E7," *Ann. Rheum. Dis.*, vol. 58(Suppl. 1):170-172 (1999).
Keystone, Edward et al., "The Armada Trial: A Double-Blind Placebo Controlled Trial of the Fully Human Anti-TNF Monoclonal Antibody, Adalimumab (D2E7), in Patients with Active RA on Methotrexate (MTX)," *Arthritis & Rheumatism*, vol. 44(9):S213 (2001).
Keystone, E. et al., "Response to Adalimumab in Patients with Early Versus Late Rheumatoid Arthritis (RA)," *Ann. Rheum. Dis.*, vol. 62(Suppl. 1):170 (2003).
Keystone, E. et al., "Adalimumab Inhibits the Progression of Structural Joint Damage in Patients with Active RA," *Ann. Rheum. Dis.*, vol. 62(Suppl. 1):64-5 (2003).
Keystone, Edward et al., "Sustained Radiographic Inhibition with Adalimumab (HUMIRA™) over 2 years in Patients with Long Standing Rheumatoid Arthritis (RA)," *Arthritis Rheum.*, vol. 48(Suppl. 9):S315 (2003).
Keystone, E. et al., "The Fully Human Anti-TNF Monoclonal Antibody, Adalimumab (D2E7), Dose Ranging Study: The 24-Week Clinical Results in Patients with Active RA on Methotrexate Therapy (The ARMADA Trial)," *Presented at the Annual Meeting of the European League Against Rheumatoid Arthritis (EULAR)*, Prague, Czech Republic, (2001).
Keystone, E.C. et al., "Subgroup Analysis of Radiographic Progression in RA Patients with Moderate Disease Treated with Adalimumab (HUMIRA®)," *Ann. Rheum. Dis.*, vol. 62(Suppl. 1):169 (2003).
Keystone, E. et al., "Efficacy and safety of Adalimumab (D2E7), the fully human anti-TNF monoclonal antibody, in MTX partial responders: Results of the 24-week ARMADA trial," *JCR: Journal of Clinical Rheumatology*, vol. 8(3):S69 (2002).
Kremer, Joel M., "Rational Use of New and Existing Disease-Modifying Agents in Rheumatoid Arthritis," *Ann. Intern. Med.*, vol. 134:695-706 (2001).
Lerner, R.A. et al. "Antibodies without immunization" *Science*, 258:1313-14 (1992).
Leusch, H-G. et al. "Failure to demonstrate TNFa-specific autoantibodies in human sera by ELISA and Western blot" *J. Immunol. Methods*, 139:145-47 (1991).
Lewis et al. "Use of alanine scanning mutagenesis to improve the affinity of an anti gp120 (HIV) antibody." *J. Cell. Biochem.*, 18D:215 (1994).
Low, Nigel M., thesis extract, Cambridge University (1996).
Low, Nigel M. et al., "Mimicking Somatic Hypermutation: Affinity Maturation of Antibodies Displayed on Bacteriophage Using a Bacterial Mutator Strain," *J. Mol. Biol.*, vol. 260:359-368 (1996).
Machold, Klaus P. et al., "Adalimumab—a new TNF-α antibody for treatment of inflammatory joint disease," *Expert Opin. Biol. Ther.*, vol. 3(2):351-360 (2003).
Marks, J.D. et al. "By-passing immunization: Human antibodies from V-gene libraries displayed on phage" *J. Mol. Biol.* 222:581-97 (1991).
Massarotti, E.M. et al., "Treatment Patterns in Early-onset Rheumatoid Arthritis (RA): Results from the Sonora Study," *Ann. Rheum. Dis.*, vol. 61(Suppl. I):S93 (2002).
Maksymowych, Walter P. et al., "Canadian Rheumatology Association Consensus on the Use of Anti-Tumour Necrosis Factor-a Directed Therapies in the Treatment of Spondyloarthritis," *The Journal of Rheumatology*, vol. 30:1356-1363 (2003).
Marzo-Ortega, Helena et al., "Inhibition of tumor necrosis factor alpha and ankylosing spondylitis," *New England Journal of Medicine*, vol. 248(4):359-360 (2003).
Medynski, Dan, "Phage Display: All Dressed UP and Ready to Role," *Bio/Technology*, vol. 12:1134-1136(1994).
Möller, A. et al. "Monoclonal antibodies to human tumor necrosis factor a: in vitro and vivo application" *Cytokine*, 2(3):162-69 (1990).
Nilsson, Björn, "Antibody engineering," *Current Opinion in Structural Biology*, vol. 5:450-456 (1995).
Osbourn, Jane et al., "From rodent reagents to human therapeutics using antibody guided selection," *Methods*, vol. 36:61-68 (2005).
Pham, T. et al., "Initiation of biological agents in patients with ankylosing spondylitis: results of a Delphi study by the ASAS Group," *Ann. Rheum. Dis.*, vol. 62:812-816 (2003).
Pincus, Theodore et al, "Combination Therapy with Multiple Disease-Modifying Antirheumatic Drugs in Rheumatoid Arthritis: A Preventive Strategy," *Ann. Intern. Med.*, vol. 131:768-774 (1999).

(56) References Cited

OTHER PUBLICATIONS

Queen, Cary et al., "A humanized antibody that binds to the interleukin 2 receptor," *Proc. Natl. Acad. Sci. USA*, vol. 86:10029-10033 (1989).
Rau, Rolf et al., "Long-term efficacy and tolerability of multiple I.V. doses of the fully human Anti-TNF-Antibody D2E7 in patients with Rheumatoid Arthritis," *Arthritis & Rheumatism*, vol. 41(Suppl.):S55, No. 137 (1998).
Rau, R. et al., "Erfahrungen mit D2E7," *Akt. Rheumatol.*, vol. 25:83-88 (2000).
Rau, R. et al., "2.5-Year Treatment Results with Adalimumab (D2E7), the First Fully Human Anti-TNF Monoclonal Antibody, in Combination with Methotrexate in Active Rheumatoid Arthritis," *Ann. Rheum. Dis.*, vol. 61(Suppl. 1):S55 (2002).
Rau, R. et al., "Kombinationstheraipe mit dem humanen Anti-TNF-Antikörper D2E7 and Methotrexat bei aktiver chronischer Polyarthritis," *Z. Rheumatol.*, vol. 58(Suppl. 1):1/35, F20 (1999).
Rau, R., "Erfahrungen mit D2E7," *Z. Rheumatol.*, vol. 58(Suppl. 1):1/21, S51 (1999).
Rau, R. et al., "Wirkung under Verträglichkeit wiederholter intravenöser Gaben der humanen anti-TNF Antikörpers D2E7 bei Patienten mit chronischer Polyarthritis," *Z. Rheumatol.*, vol. 58(Suppl. 1):1/41, p. 12 (1999).
Rau, R. et al., "Treatment with Adalimumab (D2E7), the Fully Human Anti-TNF Monoclonal Antibody, Slows Radiographic Disease Progression in Rheumatoid Arthritis: Results of a 12-Month Study," *J. Clin. Rheum.*, vol. 8(Suppl.):S78 (2002).
Rau, R. et al., "Adalimumab Inhibits Radiographic Disease Progression in Long-Standing, Rapidly Progressive Rheumatoid Arthritis," *Ann. Rheum. Dis.*, vol. 62(Suppl. 1):191 (2003).
Rau, R., "Adalimumab (a fully human anti-tumour necrosis factor α monoclonal antibody) in the treatment of active rheumatoid arthritis: the initial results of five trials," *Ann. Rheum. Dis.*, vol. 61(Suppl. II):ii70-ii73 (2002).
Rau, R. et al., "Long-term Treatment with the Fully Human Anti-TNF-Antibody D2E7 Slows Radio-graphic Disease Progression in Rheumatoid Arthritis," *Arthritis and Rheumatism*, vol. 42(9):S400 (1999).
Reimold, Andreas M., "New Indications for Treatment of Chronic Inflammation by TNF-a Blockade," *The American Journal of Medical Science*, vol. 325(2):75-92 (2003).
Reinhart, Konrad et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," *Crit. Care. Med.*, vol. 24(5):733-742 (1996).
Revicki, D. et al., "Treatment with Adalimumab (D2E7), a Fully Human Anti-TNF Monoclonal Antibody, Improves Physical Function, Vitality, and Mental Health While Reducing Bodily Pain in Patients with Active Rheumatoid Arthritis (RA)," *Arthritis Rheum.*, vol. 46(9 Suppl.):S537 (2002).
Riechmann, Lutz et al., "Phage Display and Selection of a Site-Directed Randomized Single-Chain Antibody Fv Fragment for Its Affinity Improvement," *Biochemistry*, vol. 32:8848-8855 (1993).
Salfeld, J. et al., "Generation of Fully Human Anti-TNF Antibody D2E7," *Arthritis Rheum.*, vol. 41(9 Suppl.):S57 (1998).
Santora, L.C. et al., "Characterization of Noncovalent Complexes of Recombinant Human Monoclonal Antibody and Antigen Using Carbon Exchange, Size Exclusion Chromatography, and BIAcore," *Analytical Biochemistry*, vol. 299(2):119-129 (2001).
Santora, L.C. et al., "Characterization of Recombinant Human Monoclonal Tissue Necrosis Factor-α Antibody Using Cation-Exchange HPLC and Capillary Isoelectric Focusing," *Analytical Biochemistry*, vol. 275:98-108 (1999).
Schattenkirchner, M. et al., "Long-term Use of the Fully Human Anti-TNF Antibody D2E7 in Combination with Methotrexate in Active Rheumatoid Arthritis," *Presented at: The Annual Meeting of the European League Against Rheumatism*, p. S228 (2000).
Schattenkirchner, M. et al., "Long-term Use of the Fully Human Anti-TNF Antibody Adalimumab (D2E7) in Dmard-refractory Rheumatoid Arthritis," Presented at: The Annual Meeting of the European League Against Rheumatism (EULAR), Prague, Czech Republic, Jun. 2001.
Schattenkircher, M. et al., "Phase-1-Studies zur Wirksamkeit und Verträglichkeit Wöchentlicher subcutaner Injekttionen des humanen Anti-TNF-Antikörpers D2E7 bei cP," *Z. Rheumatol.*, vol. 58(Suppl. 1):1/42, p. 14 (1999).
Schattenkirchner, M. et al, "Efficacy and Tolerability of Weekly Subcutaneous Injections of the Fully Human Anti-TNF-Antibody D2E7 in Patients with Rheumatoid Arthritis—Results of a Phase I Study," *Arthritis and Rheumatism*, vol. 41(9):S57 (1998).
Schiff, M. et al., "Rates of Infection in Adalimumab Rheumatoid Arthritis Clinical Trials," *Ann. Rheum. Dis.*, vol. 62(Suppl. 1):184 (2003).
Schiff, M. et al., "A Randomized, Controlled, Safety Trial of Adalimumab (D2E7), a Fully Human Anti-TNF Monoclonal Antibody, Given to RA Patients in Combination with Standard Rheumatologic Care: The STAR (Safety Trial of Adalimumab in Rheumatoid Arthritis) Trial," *Ann. Rheum. Dis.*, vol. 61(Suppl. 1):S169 (2002).
Schiff, M. et al., "Efficacy of Adalimumab Measured by the Disease Activity Score 28 (DAS28) and EULAR Response Criteria," *Ann. Rheum. Dis.*, vol. 62(Suppl. 1):170 (2003).
Schiff, Michael A. et al., "Malignancies in Rheumatoid Arthritis (RA) Clinical Trials with Adalimumab (HUMIRA™)," *Arthritis Rheum.*, vol. 48(Suppl. 9):S700 (2003).
Schiff, Michael H. et al., "Sustained Efficacy of Adalimumab (HUMIRA™) Plus Methotrexate in Rheumatoid Arthritis (RA) Patients," *Arthritis Rheum.*, vol. 48(Suppl. 9):S314 (2003).
Schnarr, S. et al., "Anti-tumour necrosis factor (TNF)-a therapy in undifferentiated spondyloarthropathy," *Clin. Exp. Rheumatol.*, vol. 20(Suppl. 28):S126-S129 (2002).
Sibilia, Jean, "Combinaison de traitements de fond dans la polyarthrite rhumatoïde," *Ann. Med. Interne.*, vol. 153(1):41-52 (2002).
Siegel, Jeffrey N. et al., "Evidence of Effects of a TNF Blocking Agent in ACR20 Non-Responders," *Arthritis Rheum.*, vol. 48(Suppl. 9):S127 (2003).
Sieper, J. et al., "New treatment options in ankylosing spondylitis: a role for anti-TNFa therapy," *Ann. Rheum.*, vol. 60:iii58-iii61 (2001).
Smith, David Lloyd et al., "Ibuprofen in psoriatic arthritis," *Arthritis Rheum.*, vol. 23(8):961-962 (1980).
Smolen, Josef S. et al., "Objectives and Strategies for Rheumatoid Arthritis Therapy: Yesterday vs. Today," *Drugs of Today*, vol. 39(Suppl. B):3-8 (2003).
Smolen, J.S. et al., "A Comparison of the SDAI and DAS28 as Measures of Response in Adalimumab (HUMIRA™) Clinical Trials in Rheumatoid Arthritis (RA)," *Arthritis Rheum.*, vol. 48(Suppl. 9):S107 (2003).
Stokes, David G. et al., "Potential of Tumor Necrosis Factor Neutralization Strategies in Rheumatologic Disorders Other Than Rheumatoid Arthritis," *Seminars in Arthritis and Rheumatism*, vol. 33(1):1-18 (2003).
Stone, Millicent et al., "Clinical and Imaging Correlates of Response to Treatment with Infliximab in Patients with Ankylosign Spondylitis," *J. Rheumatol.*, vol. 28:1605-1614 (2001).
Strand, V. et al., "Treatment with Adalimumab (D2E7), a Fully Human Anti-TNF Monoclonal Antibody, Improves Physical Function and Health Related Quality of Life (HRQOL) in Patients with Active Rheumatoid Arthritis (RA)," *Ann. Rheum. Dis.*, vol. 61(Suppl. I):S175 (2002).
Strand, Vibeke et al., "Improvement in Health-related Quality of Life, Health Utility, and Fatigue in Patients with Active Rheumatoid Arthritis (RA) on Adalimumab (HUMIRA™, Abbott) Therapy," *Arthritis Rheum.*, vol. 48(Suppl. 9):S402 (2003).
Strand, V. et al., "Adalimumab Improves Health-related Quality of Life in Rheumatoid Arthritis Patients," *Ann. Rheum. Dis.*, vol. 62(Suppl. 1):356 (2003).
Thomas, Clayton L., Taber's Cyclopedic Medical Dictionary, F.A. Davis Company, pp. 118-119 (1977).
Thompson, Julia et al., "Affinity Maturation of a High-affinity Human Monoclonal Antibody Against the Third Hypervariable Loop

(56) References Cited

OTHER PUBLICATIONS of Human Immunodeficiency Virus: Use of Phage Display to Improve Affinity and Broaden Strain Reactivity," *J. Mol. Biol.*, vol. 256:77-88 (1996).

Tomlinson, Ian M. et al., "The Repertoire of Human Germline $V_H$ Sequences Reveals about Fifty Groups of $V_H$ Segments with Different Hypervariable Loops," *J. Mol. Biol.*, vol. 227:776-798 (1992).

Tomlinson, Ian M. et al., "The structural repertoire of the human $V_k$ domain," *The EMBO Journal*, vol. 14( 18):4628-4638 (1995).

Tracey, Kevin J. et al., "Tumor Necrosis Factor: A Pleiotropic Cytokine and Therapeutic Target," *Annu. Rev. Med.*, vol. 45:491-503 (1994).

Tugwell, P. et al., "Adalimumab Improves Utility and Quality-adjusted Life Days in Rheumatoid Arthritis," *Ann. Rheum. Dis.*, vol. 62(Suppl. 1):107-8 (2003).

Tugwell, P. et al., "Relationship Between ACR Response and HRQL in Adalimumab Clinical Trials," *Ann. Rheum. Dis.*, vol. 62(Suppl. 1):536 (2003.

Vajdos, Felix F. et al., "Comprehensive Functional Maps of the Antigen-binding Site of an Anti-ErbB2 Antibody Obtained with Shotgun Scanning Mutagenesis," *J. Mol. Biol.*, vol. 320:415-428 (2002).

van de Putte, L.B.A. et al., "One Year Efficacy Results of the Fully Human Anti-TNF Antibody D2E7 in Rheumatoid Arthritis," *Arthritis Rheum.*, vol. 43(9 Suppl.):S269 (2000).

Van De Putte, L.B. et al., "Adalimumab (D2E7), the Fully Human Anti-TNF Monoclonal Antibody, in the Treatment of Patients with Rheumatoid Arthritis Who Failed Previous DMARD Therapy: Efficacy and Safety Results from a 6-Month Phase III Study," *JCR: Journal of Clinical Rheumatology*, vol. 8(Suppl. 3):S89 (2002).

Van de Putte, Atkins Malaise et al., "Adalimumab (D2E7) Monotherapy in the Treatment of Patients with Severely Active Rheumatoid Arthritis (RA)," *Arthritis Rheum.*, vol. 46(9 Suppl.):S171 (2002).

van de Putte, B.A. et al., "Efficacy of the Fully Human anti-TNF Antibody D2E7 in Rheumatoid Arthritis," *Arthritis & Rheumatism*, vol. 42(9):S400, No. 1977 (1999).

van de Putte, L.B.A. et al., "Eine placebo-kontrollierte Phase-1-Studie des humanen Anti-TNF-Antikörpers D2E7 bei Patienten mit aktiver chronischer Polyarthritis," *Z. Rheumatol.*, vol. 58(Suppl. 1):1/34, F19 (1999).

Van de Putte, L.B.A. et al., "Efficacy and Safety of Adalimumab (D2E7), the First Fully Human Anti-TNF Monoclonal Antibody, in Patients with Rheumatoid Arthritis Who Failed Previous DMARD Therapy: 6-Month Results from a Phase III Study," *Ann. Rheum.. Dis.*, vol. 61(Suppl. 1):S168 (2002).

van de Putte, Leo, et al., "Adaliumumab," TNFα-Inhibition in the Treatment of Rheumatoid Arthritis, MD Martin Dunitz, Larry W. Moreland, Ed., pp. 71-93 (2003).

van de Putte, L.B.A. et al., "Sustained 5-Year Efficacy of Adalimumab (HUMIRA™) Monotherapy in DMARD-Refractory rheumatoid arthritis (RA)," *Arthritis Rheum.*, vol. 48(Suppl. 9):S314 (2003).

van de Putte, L.B.A. et al., "Efficacy and safety of the fully human anti-tumour necrosis factor α monoclonal antibody adalimumbo (D2E7) in DMARD refractory patients with rheumatoid arthritis: a 12 week, phase II study," *Ann. Rheum. Dis.*, vol. 62:1168-1177 (2003).

Van de Putte, Leo B.A. et al., "A Single Dose Placebo Controlled Phase I Study of the Fully Human Anti-TNF Antibody D2E7 in Patients with Rheumatoid Arthritis," *Arthritis Rheum.*, vol. 41:S57 (1998).

Van den Bosch, Filip et al., "Crohn's disease associated with spondyloarthropathy: effect of TNF-a blockade with infliximab on articular symptoms," *The Lancet*, vol. 356(9244):1821-1822 (2000).

van der Poll, T. et al., "Effect of postponed treatment with an anti-tumour necrosis factor (TNF) F(ab')2 fragment on endotoxin-induced cytokine and neutrophil responses in chimpanzees," *Clin. Exp. Immunol.*, vol. 100:21-25 (1995).

van Riel, P.L.C. et al., "Long-Term Treatment with Adalimumab (D2E7) Using Background Methotrexate in Active Rheumatoid Arthritis: Results of a 3 Year Study," *Arthritis Rheum.*, vol. 46(9 Suppl.):S534 (2002).

Vaughan, Tristan J. et al., "Human antibodies by design," *Nature Biotechnology*, vol. 16:535-539 (1998).

Velagapudi, R.B. et al., "Pharmacokinetics of Adalimumab (D2E7), a Fully Human Anti-TNF-α Monoclonal Antibody, Following a Single Intravenous Injection in Rheumatoid Arthritis Patients Treated with Methotrexate," *Arthritis Rheum.*, vol. 46(9 Suppl.):S133 (2002).

Velagapudi, Raja B. et al., "Effect of Methotrexate (MTX) Coadministration on the Pharmacokinetics (PK) of Adalimumab (HUMIRA™, Abbott) Following a Single Intravenous (iv) Injection," *Arthritis Rheum.*, vol. 48(Suppl. 9):S141 (2003).

Ward, E. Sally et al., "Binding activities of a repertoire of single immunoglobulin variable domains secreted from *Escherichia coli*," *Nature*, vol. 341:544-546 (1989).

Weinblatt, M. et al., "The ARMADA Trial: Efficacy and Safety of Adalimumab in Patients with Active RA at 24 Months," *Ann. Rheum. Dis.*, vol. 62(Suppl. 1):98 (2003).

Weinblatt, Michael E. et al., "The ARMADA Trial: Sustained Improvement and Tolerability in Long-Term Follow-Up of Patients Treated with Adalimumab (HUMIRA™)," *Arthritis Rheum.*, vol. 48(Suppl. 9):S314 (2003).

Weinblatt, Michael E. et al., "Adalimumab, a Fully Human Anti-Tumor Necrosis Factor α Monoclonal Antibody, for the Treatment of Rheumatoid Arthritis in Patients Taking Concomitant Methotrexate," *Arthritis & Rheumatism*, vol. 48(1):35-45 (2003).

Weisman, M.H. et al., "The Importance of Pain and the Impact of Adalimumab on Pain in RA Patients," *Ann. Rheum. Dis.*, vol. 62(Suppl. 1):351 (2003).

Weisman, Michael et al., "A Dose Escalation Study Designed to Demonstrate the Safety, Tolerability and Efficacy of the Fully Human Anti-TNF Antibody, D2E7, Given in Combination with Methotraxate," *Arthritis Rheum.*, vol. 43(9 Suppl.):S391 (2000).

Weisman, Michael H. et al., "Efficacy, Pharmacokinetic, and Safety Assessment of Adalimumab, a Fully Human Anti-Tumor Necrosis Factor-Alpha Monoclonal Antibody, in Adults with Rheumatoid Arthritis Receiving Concomitant Methotrexate: A Pilot Study," *Clinical Therapeutics*, vol. 25(6):1700-1721 (2003).

Wellbome, F. et al., "Adalimumab (D2E7), a Fully Human Anti-TNF-α Monoclonal Antibody, Improved Health-Related Quality of Life in Patients with Active Rheumatoid Arthritis Despite Concomitant Methotrexate Therapy," *Arthritis Rheum.*, vol. 46(9 Suppl.):S518 (2002).

Wells, A.F. et al., "Incidence of Injection-Site Reactions Associated with Adalimumab (D2E7) Give Subcutaneously for at Least 6 Months: A Retrospective Analysis of 4 Phase II/III Clinical Trials," *Arthritis Rheum.*, vol. 46(9 Suppl.):S171 (2002).

Wells, A.F. et al., "Injection-site Reactions in Adalimumab Rheumatoid Arthritis (RA) Pivotal Clinical Trials," *Ann. Rheum. Dis.*, vol. 62(Suppl. 1):411 (2003).

Winter, Greg et al., "Making Antibodies by Phage Display Technology," *Annu. Rev. Immunol.*, vol. 12:433-455 (1994).

Winter, Greg et al, "Humanized antibodies," *Immunology Today*, vol. 14(6):243-246 (1993).

Zou, J.X. et al., "Immunological basis for the use of TNF-a-blocking agents in ankylosing spondylitis and immunological changes during treatment," *Clin. Exp. Rheumatol.*, vol. 20(Suppl. 28):S34-S37 (2002).

Aboulafia, D., "Etanercept for the treatment of human immunodeficiency virus associated psoriatic arthritis," Mayo Clinic Proceedings, 75(10): 1093 1098. (2002).

Antoni, C., et al., "Open label study of infliximab treatment for psoriatic arthritis: clinical and magnetic resonance imaging measurements of reduction of inflammation," Arthritis & Rheumatism, vol. 47(5): 506 512. (2002).

Barrera P., et al., "Effects of treatment with a fully human anti-tumour necrosis factor α monoclonal antibody on the local and systemic homeostasis of interleukin 1 and TNFα in patients with rheumatoid arthritis," *Ann. Rheum Dis.*; vol. 60:660-669 (2001).

(56) References Cited

OTHER PUBLICATIONS

Bennett, A.N. "Adalimumab in clinical practice. Outcome in 70 rheumatoid arthritis patients, including comparison of patients with and without previous anti-TNF exposure." Rheumatology 44:1026-1031 (2005).
Borigini, M., et al., "Innovative Treatment Approaches for rheumatoid arthritis. Combination Therapy," *Baillière's Clinical Rheumatology*, vol. 9, 4: 689-710 (1995).
Brocq et al. "Adalimumab in rheumatoid arthritis after failed infliximab and/or etanercept therapy: experience with 18 patients" Joint Bone Spine 2004; 71:601-603. (2004).
Carlin, CS, et al., "A 50% reduction in the psoriasis area and severity index (PASI.50) is a clinically significant endpoint in the assessment of psoriasis," *Journal of the American Academy of Dermatology*, vol. 50, 6: 859-866 (2003).
Cella, D. Validation of the Functional Assessment of Chronic Illness Therapy-Fatigue (FACIT-F) in the Safety Trial of Adalimumab (D2E7) in Rheumatoid Arthritis (STAR). Arthritis Rheum 2002;46(9)(Suppl):S115 (Abst 208).
Cherouvim, E.P. et al., "Infliximab Therapy for Patients With Active and Refractory Spondyloarthropathies at the Dose of 3 mg/kg," *J. Clin. Rheumatol.*, vol. 10:162-168 (2004).
Davison, SC, et al., "Etanercept for severe psoriasis and psoriatic arthritis: observations on combination therapy," *British Journal of Dermatology*, vol. 147, 4:831-2 (2002).
De Keyser, Filip et al., "Anti-TNF-alpha therapy in ankylosing spondylitis," *Cytokine*, vol. 33:294-298 (2006).
Elkayam, O., et al., "From wheels to feet: a dramatic response of severe chronic psoriatic arthritis to etanercept," Ann. Rheumatic Diseases, vol. 59: 839. (2000).
Genovese, MC, et al., "Adalimumab Efficacy in Patients with Psoriatic Arthritis Who Failed Prior DMARD Therapy," Ann Rheum Dis 2005; 64(Suppl III): 313 [FRI0187].
Iyer, S., et al., "Etanercept for severe psoriasis and psoriatic arthritis: observations on combination therapy," British Journal of Dermatology, vol. 146: 118 121. (2002).
Kavanaugh, AF, et al. "Adalimumab Treatment With and Without Methotrexate in Patients with Moderate to Severe Psoriatic Arthritis: Results from ADEPT", Ann Rheum Dis 2005; 64(Suppl III):325 [FRI0227].
Kietz, DA, et al. "Clinical Response to Etanercept in Polyarticular Course Juvenile Rheumatoid Arthritis", J Rheum, 28(2):360-362, Feb. 2001.
Kurschat, P., et al., "Treatment of psoriatic arthritis with etanercept," J Am Acad Dermatology, vol. 44(6): 1052. (2001).
Lipsy, R., "Etanercept and its implications for managed care," Am J of Managed Care, vol. 8(6), S194 S200. (2002).
Lipsky, PE, et al., "Infliximab and Methotrexate in the Treatment of Rheumatoid Arthritis," *The New England Journal of Medicine*; vol. 343 22:1594-1602 (2000).
Maini, R., et al., "Infliximab (chimeric anti-tumour necrosis factor α monoclonal antibody) versus placebo in rheumatoid arthritis patients receiving concomitant methotrexate: a randomised phase III trial," *The Lancet*, vol. 354:1932-39 (1999).
Marks, JD, et al., "By-Passing Immunization: Building High Affinity Human Antibodies by Chain Shuffling," *Nature Biotechnology*, vol. 10: 779-783 (1992).
Mease, P. J., "Adalimumab: an anti-TNF agent of the treatment of psoriatic arthritis" Expert Opinion Biol Ther 5(11): 1491-1504 (2005).
Mease, P.J., "Cytokine blockers in psoriatic arthritis," Ann Rheum Dis, vol. 60:iii37 iii40. (2001).
Mease, P.J., et al., "Etanercept in the treatment of psoriatic arthritis and psoriasis: a randomised trial," Lancet, vol. 356(9227): 385 390. (2000).
Mease, P.J., "Etanercept: A new era in the treatment of psoriatic arthritis," Am J of Managed Care, vol. 8(6): S181 S193. (2002 ).
Mease, PJ, "Tumour necrosis factor (TNF) in psoriatic arthritis: pathophysiology and treatment with TNF inhibitors," *Ann Rheum Dis.*, vol. 61:298-304 (2002).
Paulus, H., et al., "Relative contributions of the components of the American College of Rheumatology 20% criteria for improvement to responder status in patients with early seropositive rheumatoid arthritis," *Arthritis & Rheumatism*; vol. 43(12): 2743-2750 (2000).
Ricardo, R.Clinical benefits in patients with psoriasis after Efalizumab therapy: Clinical trial versus practice. Cutis 74:193-200. (2004).
Rinehart-Kim, J., et al., "Alterations in the Gene Expression Profile of MCF-7 Breast Tumor Cells in Response to c-Jun," *Int. J. Cancer*, vol. 88:180-190 (2000).
Roberts, L. et al., "Tumour necrosis factor inhibitors: risks and benefits in patients with rheumatoid arthritis," *Int. Med. J.*, vol. 34:687-693 (2004).
Sandborn, W. "Antitumor necrosis factor for inflammatory bowel disease: A Review of agents, pharmacology, clinical results, and safety." Inflamm. Bowel Disease 5(2): 199-33 (1999).
Stockinger, H., "CD147," http://mpr.nci.nhi.gov; (1999).
Taylor, P., "Anti-tumor necrosis factor therapies," *Current Opinion in Rheumatology*, vol. 13:164-169 (2001).
Van Assche, G. "Anti-TNF agents in Crohn's Disease." Expert Opin Investig. Drugs; 9 (1):103-11. (2000).
Van de Putte, et al., "Efficacy and safety of adalimumab as monotherapy in patients with rheumatoid arthritis for whom previous disease modifying antirheumatic drug treatment has failed," *Ann. Rheum Dis.*; vol. 63:508-516 (2004).
Van Riel, PL. "A Comparison of CRP and ESR to Measure the DAS28 in Adalimumab Clinical Trials." Ann Rheum Dis 2003;62(Suppl I:169-70 (Poster THU0199). (2003).
Wailoo, A., et al., "Modeling the cost effectiveness of etanercept, adalimumab and anakinra compared to infliximab in the treatment of patients with rheumatoid arthritis in the medicare program," *Agency for Healthcare Research and Quality*, (2006).
Yazici, Y., et al., "A preliminary study of etanercept in the treatment of severe, resistant psoriatic arthritis," Clinical and Experimental Rheumatology, vol. 18:732 734. (2000).
Yazici, Y., et al., "Etanercept in the treatment of severe, resistant psoriatic arthritis: Continued efficacy and changing patterns of use after two years," J Am Acad Dermatology, vol. 44(6): 1052. (2001).
Bang, L. et al.: "Adalimumab—A review of its use in rheumatoid arthritis." *Biodrugs*, vol. 18, No. 2, 2004, pp. 121-139.
Doring et al. "Identification and Characterization of a TNFα Antagonist Derived From a Monoclonal Antibody" *Mol. Immunol.* (1994) vol. 31: 1059 (1994).
Elliott, MJ et al. "Suppression of Fever and the Acute-Phase Response in a Patient With Juvenile Chronic Arthritis Treated with Monoclonal Antibody to Tumour Necrosis Factor-alpha (Ca2)" *British Journal of Rheumatology*, vol. 36, Jan. 1, 1997, pp. 589-593.
Fleischmann, R. et al. "Developing a new generation of TNF-alpha antagonists for the treatment of rheumatoid arthritis." *Molecular Interventions*, Sep. 2003, vol. 3, No. 6, Sep. 2003 pp. 310-318.
Genovese, M. et al. "Treatment of Rheumatoid Arthritis with Etanercept." *Rheum Dis Clin N Am* 30: 311-328 (2004).
Keffer, J. et al. "Transgenic Mice 1 Expressing Human Tumour Necrosis Factor: A Predictive Genetic Model of Arthritis" *EMBO (European Molecular Biology Organization) Journal*, vol. 10, No. 13, 1991, pp. 4025-4031.
Li et al. "The TNF-alpha transgenic mouse model of inflammatory arthritis." *Springer Seminars in Immunopathology*, vol. 25, No. 1, Aug. 2003, pp. 19-33.
Maksymowych, W. "Update on the treatment of ankylosing spondylitis." *Therapeutics and Clinical Risk Management* 3(6):1125-1133 (2007).
Marks, J. et al. "By-Passing Immunization: Building High Affinity Human Antibodies by Chain Stuffing." *Nature Biotechnology* 10:779-783 (1992).
Mease, PJ et al. "Adalimumab for the treatment of patients with moderately to severely active psoriatic arthritis: results of a double-blind, randomized, placebo-controlled trial." *Arthritis and Rheumatism* Oct. 2005, vol. 52, No. 10, pp. 3279-3289.
Mease, PJ et al: "Psoriatic Arthritis Treatment: Biological Response Modifiers." *Annals of the Rheumatic Diseases*. vol. 64 Suppl 2, Mar. 2005. pages ii78-ii82.

(56) References Cited

OTHER PUBLICATIONS

Nash, P. et al. "Psoriatic arthritis therapy: NSAIDS and traditional DMARDs." *Ann Rheum Dis* 64(Suppl II):ii74-ii77 (2005).

Rader et al. "A phage display approach to rapid antibody humanization: Designed combinatorial V gene libraries" *Proc Natl Acad Sci USA* 95:8910-8915 (1998).

Shealy, DJ et al. "Anti-TNF-alpha antibody allows healing of joint damage in polyarthritic transgenic mice" *Arthritis Research, Current Science*, vol. 4, No. 5, Jun. 28, 2002, p. R7.

Thorp, K et al. "Tumour necrosis factor induction of ELAM-1 and ICAM-1 on human umbilical vein endothelial cells—analysis of tumour necrosis factor-receptor interactions." *Cytokine* 4(4): 313 (1992).

* cited by examiner

USE OF HUMAN TNFα ANTIBODIES FOR TREATMENT OF EROSIVE POLYARTHRITIS

RELATED APPLICATIONS

This application claims priority to U.S. Provisional Appln. No. 60/681,645, which was filed on May 16, 2005.

This application is related to U.S. Pat. Nos. 6,090,382, 6,258,562, and 6,509,015. This application is also related to U.S. patent application Ser. No. 09/801,185, filed Mar. 7, 2001, now U.S. Pat. No. 7,223,394; U.S. patent application Ser. No. 10/163,657, filed Jun. 5, 2002; and U.S. patent application Ser. No. 10/422,287, filed Apr. 26, 2002; U.S. patent application Ser. No. 10/525,292, filed Aug. 16, 2002; U.S. patent application Ser. No. 10/693,233, filed Oct. 24, 2003; U.S. patent application Ser. No. 10/622,932, filed Jul. 18, 2003; U.S. patent application Ser. No. 10/623,039, filed Jul. 18, 2003; U.S. patent application Ser. No. 10/623,076, filed Jul. 18, 2003; U.S. patent application Ser. No. 10/623,065, filed Jul. 18, 2003, now abandoned; U.S. patent application Ser. No. 10/622,928, filed Jul. 18, 2003, now abandoned; U.S. patent application Ser. No. 10/623,075, filed Jul. 18, 2003, now abandoned; U.S. patent application Ser. No. 10/623,035, filed Jul. 18, 2003, now abandoned; U.S. patent application Ser. No. 10/622,683, filed Jul. 18, 2003, now abandoned; U.S. patent application Ser. No. 10/622,205, filed Jul. 18, 2003, now abandoned; U.S. patent application Ser. No. 10/622,210, filed Jul. 18, 2003, now abandoned; and U.S. patent application Ser. No. 10/623,318, filed Jul. 18, 2003. This application is also related to PCT/US05/12007, filed Apr. 11, 2005, published as WO 05/110452. The entire contents of each of these patents and patent applications are hereby incorporated herein by reference.

BACKGROUND OF THE INVENTION

Polyarthritis may be erosive or non-erosive. In the erosive form, the underlying disease process erodes the cartilage; in the non-erosive form, the cartilage is not affected. Erosive polyarthritis is an inflammatory disease of joints that results in tissue destruction and erosion within the affected joint. Erosive polyarthritis occurs in many patients having inflammatory disorders, including psoriatic arthritis, spondylarthropathies, such as ankylosing spondylitis, and juvenile rheumatoid arthritis. Many of the current treatments of disorders in which erosive polyarthritis is a manifestation fail to focus on decreasing radiographic progression of joint disease.

SUMMARY OF THE INVENTION

There is a need to treat erosive polyarthritis in a safe and effective manner. While traditional treatments of erosive polyarthritis, such as administration of DMARDs, may delay disease progression, traditional treatments may be slow to become effective, may lose efficacy with time, and may be associated with potentially serious toxic effects. The present invention provides a safe and effective means for treating erosive polyarthritis and slowing the progression of joint disease.

The present invention includes methods of treating erosive polyarthritis comprising administering TNF inhibitors. The invention also provides a method for treating a human subject suffering from erosive polyarthritis, comprising administering to the subject an anti-TNFα antibody, such that erosive polyarthritis is treated. Kits and articles of manufacture comprising a TNFα inhibitor are also included in the invention.

In one embodiment, the TNFα inhibitor is selected from the group consisting of an anti-TNFα antibody, or an antigen-binding portion thereof, a TNF fusion protein, or a recombinant TNF binding protein. In one embodiment, the TNF fusion protein is etanercept. In another embodiment, the anti-TNFα antibody, or antigen-binding portion thereof, is an antibody selected from the group consisting of a humanized antibody, a chimeric antibody, and a multivalent antibody. In one embodiment, the anti-TNFα antibody, or antigen-binding portion thereof, is infliximab, golimumab, or adalimumab. In still another embodiment, the anti-TNFα antibody, or antigen-binding portion thereof, is a human antibody.

The invention provides a method for treating a human subject suffering from erosive polyarthritis, comprising administering to the subject a TNFα antibody, or antigen-binding portion thereof, such that erosive polyarthritis is treated.

In one embodiment, the TNFα antibody, or antigen-binding portion thereof, is an antibody selected from the group consisting of a humanized antibody, a chimeric antibody, and a multivalent antibody. In another embodiment, the TNFα antibody, or antigen-binding portion thereof, is infliximab or golimumab.

In one embodiment, the TNFα antibody, or antigen-binding portion thereof, is a human antibody. In one embodiment, the human antibody, or an antigen-binding portion thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less. In another embodiment, the human antibody, or an antigen-binding portion thereof, has the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12. In still another embodiment, the human antibody, or an antigen-binding portion thereof, comprises a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and comprises a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. In yet another embodiment, the human antibody, or an antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2. In one embodiment, the human antibody, or an antigen-binding portion thereof, is adalimumab.

In one embodiment, the TNFα antibody, or antigen-binding portion thereof, is administered to the subject on a biweekly dosing regimen.

In one embodiment, the subject has a disorder in which TNFα activity is detrimental. In one embodiment, the disorder in which TNFα activity is detrimental is selected from the group consisting of psoriatic arthritis, ankylosing spondylitis, and juvenile rheumatoid arthritis. In another embodiment, the disorder in which TNFα activity is detrimental is psoriatic arthritis. In still another embodiment, the disorder in which TNFα activity is detrimental is rheumatoid arthritis.

In one embodiment, the invention includes further comprising administering an additional therapeutic agent to the subject. In one embodiment, the additional therapeutic agent is methotrexate. In another embodiment, the additional therapeutic agent is a Disease Modifying Anti-Rheumatic Drug (DMARD) or a Nonsteroidal Antiinflammatory Drug (NSAID) or a steroid, or any combination thereof.

The invention includes a method for testing the efficacy of a TNFα antibody, or antigen-binding portion thereof, for decreasing radiographic progression of joint disease associated with erosive polyarthritis. In one embodiment, the method for testing the efficacy of a TNFα antibody, or antigen-binding portion thereof, comprises determining the efficacy of the TNFα antibody, or antigen-binding portion thereof, using a modified Total Sharp Score (mTSS) of a patient population having joint disease associated with erosive polyarthritis and a mTSS of the patient population following administration of the TNFα antibody, or antigen-binding portion thereof, wherein no change or a decrease in the mTSS indicates that the TNFα antibody, or antigen-binding portion thereof, is efficacious for decreasing radiographic progression of joint disease associated with erosive polyarthritis. In one embodiment, the decrease in the mTSS is about –0.2.

In one embodiment, the patient population also has a disorder in which TNFα is detrimental. In one embodiment, the disorder in which TNFα activity is detrimental is selected from the group consisting of psoriatic arthritis, ankylosing spondylitis, and juvenile rheumatoid arthritis.

In one embodiment, the TNFα antibody, or antigen-binding portion thereof, is an antibody selected from the group consisting of a humanized antibody, a chimeric antibody, and a multivalent antibody. In one embodiment, the TNFα antibody, or antigen-binding portion thereof, is infliximab or golimumab. In another embodiment, the TNFα antibody, or antigen-binding portion thereof, is a human antibody. In one embodiment, the human antibody, or an antigen-binding portion thereof, dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less.

In another embodiment, the human antibody, or an antigen-binding portion thereof, has the following characteristics:
a) dissociates from human TNFα with a $K_{off}$ rate constant of $1\times10^{-3}$ s$^{-1}$ or less, as determined by surface plasmon resonance;
b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;
c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12. In still another embodiment, the human antibody, or an antigen-binding portion thereof, comprises a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and comprises a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11.

In another embodiment, the human antibody, or an antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2. In still another embodiment of the invention, the human antibody, or an antigen-binding portion thereof, is adalimumab.

In one embodiment of the invention, the TNFα antibody, or antigen-binding portion thereof, is administered to the subject on a biweekly dosing regimen. In one embodiment, antibody, or antigen-binding portion thereof, is administered in combination with an additional therapeutic agent, including, for example methotrexate The invention describes a method for monitoring the effectiveness of a TNFα antibody, or antigen-binding portion thereof, for the treatment of erosive polyarthritis in a human subject comprising determining the effectiveness of the TNFα antibody, or antigen-binding portion thereof, using a baseline modified Total Sharp Score (mTSS) of a patient population having erosive polyarthritis and a mTSS score of a patient population following administration of the TNFα antibody, or antigen-binding portion thereof, wherein a result selected from the group consisting of a decrease in the mTSS in about 9-27% of the patient population; no change in the mTSS in about 65-73% of the patient population; and an increase in the mTSS in about 9-28% of the patient population, indicates that the TNFα antibody, or antigen-binding portion thereof, is effective at treating erosive polyarthritis.

In one embodiment of the invention, the TNFα antibody, or antigen-binding portion thereof, is an antibody selected from the group consisting of a humanized antibody, a chimeric antibody, and a multivalent antibody. In one embodiment, the TNFα antibody, or antigen-binding portion thereof, is infliximab or golimumab. In another embodiment, the TNFα antibody, or antigen-binding portion thereof, is a human antibody.

In another embodiment, the human antibody, or an antigen-binding portion thereof, dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. In still another embodiment, the human antibody, or an antigen-binding portion thereof, is adalimumab.

The invention also includes a method for testing the efficacy of a TNFα antibody, or antigen-binding portion thereof, to treat erosive polyarthritis associated with psoriatic arthritis, comprising determining the efficacy of the TNFα antibody, or antigen-binding portion thereof, using a baseline modified Total Sharp Score (mTSS) and either a baseline Psoriasis Area and Severity Index (PASI) score or a baseline ACR score of a patient population having erosive polyarthritis in comparison with the mTSS and either the PASI or the ACR score of the patient population following administration of the NFα antibody, or antigen-binding portion thereof, wherein no change or a decrease in the mTSS and either an ACR20 response achieved in at least about 57% or a PASI 50 response achieved in at least about 75% of the patient population, indicates that the TNFα antibody, or antigen-binding portion thereof, is efficacious for the treatment of erosive polyarthritis associated with psoriatic arthritis. In one embodiment, an ACR50 response is achieved in at least about 39% of the patient population. In another embodiment, an ACR70 response is achieved in at least about 23% of the patient population. In still another embodiment, a PASI75 response is achieved in at least about 59% of the patient population. In yet another embodiment, a PASI90 response is achieved in at least about 42% of the patient population. In one embodiment, the TNFα antibody, or antigen-binding portion thereof, is adalimumab.

The invention describes a method for treating erosive polyarthritis comprising administering to a subject having erosive polyarthritis, adalimumab on a biweekly dosing regimen. In one embodiment, the dose of adalimumab is about 40 mg.

The invention also includes a kit comprising a pharmaceutical composition comprising a TNFα antibody, or an antigen-binding portion thereof, and a pharmaceutically acceptable carrier, and instructions for administration of the pharmaceutical composition for the treatment of erosive polyarthritis. In one embodiment, the pharmaceutical composition comprises the TNFα antibody, or antigen-binding portion thereof, adalimumab. In one embodiment, pharmaceutical composition comprises about 40 mg of adalimumab. In another embodiment, the kit further comprises an additional therapeutic agent. In one embodiment, the additional therapeutic agent is methotrexate.

The invention describes an article of manufacture comprising a packaging material; a TNFα antibody, or antigen-binding portion thereof, and a label or package insert contained within the packaging material indicating that the TNFα antibody, or antigen-binding portion thereof, can be used for the treatment of erosive polyarthritis.

The invention also includes an article of manufacture comprising a packaging material; a TNFα antibody, or antigen-binding portion thereof, and a label or package insert contained within the packaging material indicating that the TNFα antibody, or antigen-binding portion thereof, can be used for to inhibit radiographic progression of joint disease.

In one embodiment, the article of manufacture comprises an antibody selected from the group consisting of a humanized antibody, a chimeric antibody, and a multivalent antibody.

In one embodiment, the TNFα antibody, or antigen-binding portion thereof, is infliximab or golimumab. In another embodiment, the TNFα antibody, or antigen-binding portion thereof, is a human antibody. In one embodiment, the human antibody, or an antigen-binding portion thereof, dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less. In another embodiment, the human antibody, or an antigen-binding portion thereof, is adalimumab.

FIGURES

DETAILED DESCRIPTION OF THE INVENTION

I. Definitions

Figure 1A:
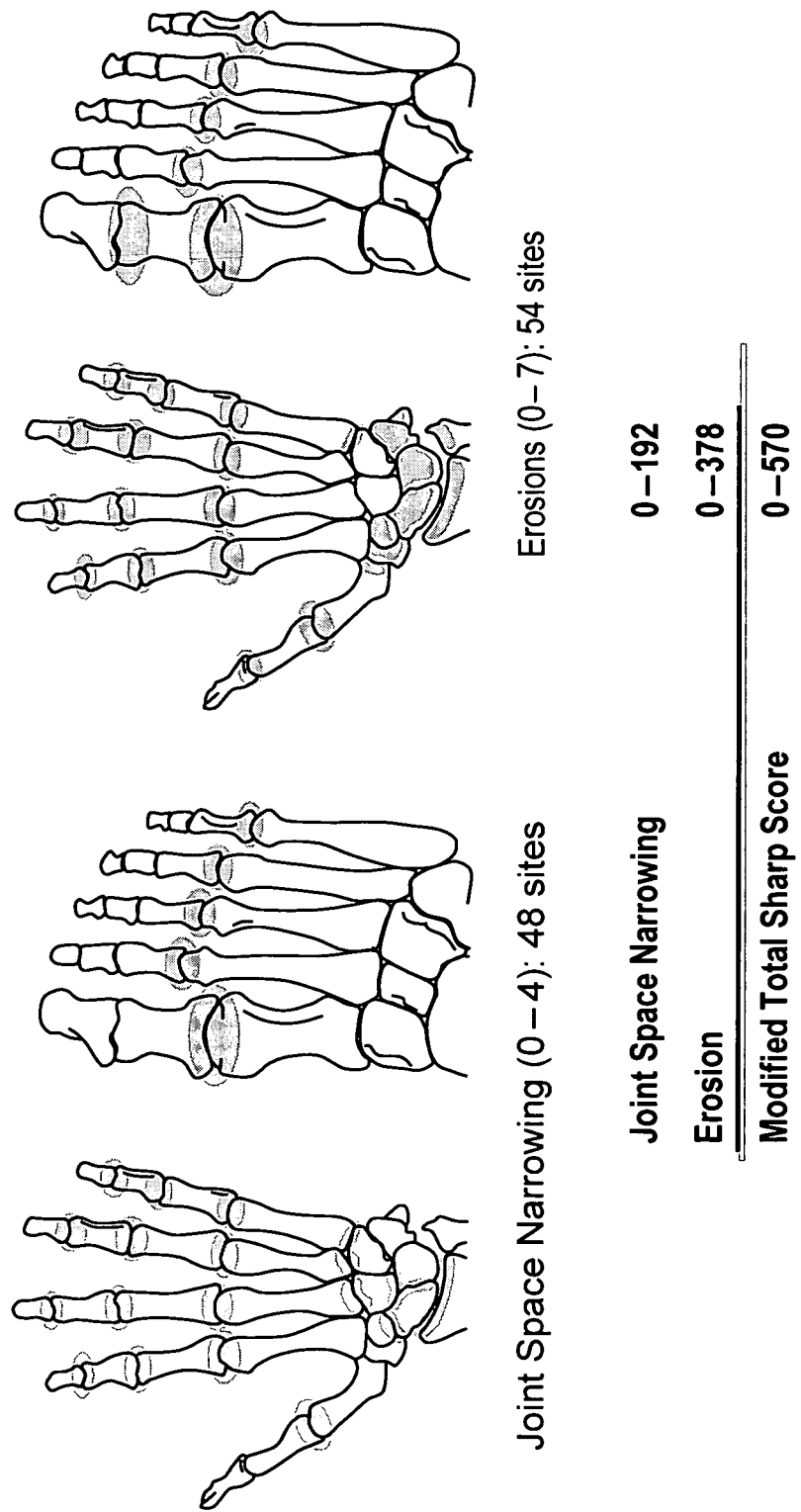
FIGS. 1a and 1b show a diagram of the modified total sharp score (mTSS) (FIG. 1a) and radiographic findings associated with PsA (FIG. 1b).

In order that the present invention may be more readily understood, certain terms are first defined.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" refers to an agent which interferes with TNFα activity. The term also includes each of the anti-TNFα human antibodies and antibody portions described herein as well as those described in U.S. Pat. Nos. 6,090,382; 6,258,562; 6,509,015, and in U.S. patent application Ser. No. 09/801,185 (now U.S. Pat. No. 7,223,394) and Ser. No. 10/302,356, now abandoned. In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451,983; and 6,448,380, each of which is incorporated by reference herein. In another embodiment, the TNFα inhibitor is a TNF fusion protein, e.g., etanercept (Enbrel®, Amgen; described in WO 91/03553 and WO 09/406,476, incorporated by reference herein). In another embodiment, the TNFα inhibitor is a recombinant TNF binding protein (r-TBP-I) (Serono).

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "antigen-binding portion" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species (discussed in further detail below). Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind hTNFα, is intended to refer to a nucleic acid molecule in which the nucleotide sequences encoding the antibody or antibody portion are free of other nucleotide sequences encoding antibodies or antibody portions that bind antigens other than hTNFα, which other sequences may naturally flank the nucleic acid in human genomic DNA. Thus, for example, an isolated nucleic acid of the invention encoding a VH region of an anti-hTNFα antibody contains no other sequences encoding other VH regions that bind antigens other than hTNFα.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "dose," as used herein, refers to an amount of TNFα inhibitor which is administered to a subject.

The term "multiple-variable dose" includes different doses of a TNFα inhibitor which are administered to a subject for therapeutic treatment. "Multiple-variable dose regimen" or "multiple-variable dose therapy" describe a treatment schedule which is based on administering different amounts of TNFα inhibitor at various time points throughout the course of treatment. In one embodiment, the invention describes a multiple-variable dose method of treatment of erosive polyarthritis comprising an induction phase and a treatment phase, wherein a TNFα inhibitor is administered at a higher dose during the induction phase than the treatment phase. Multiple-variable dose regimens are described in PCT application no. PCT/US05/12007.

The term "dosing", as used herein, refers to the administration of a substance (e.g., an anti-TNFα antibody) to achieve a therapeutic objective (e.g., the treatment of erosive polyarthritis).

The terms "biweekly dosing regimen", "biweekly dosing", and "biweekly administration", as used herein, refer to the time course of administering a substance (e.g., an anti-TNFα antibody) to a subject to achieve a therapeutic objective (e.g., the treatment of erosive polyarthritis). The biweekly dosing regimen is not intended to include a weekly dosing regimen. Preferably, the substance is administered every 9-19 days, more preferably, every 11-17 days, even more preferably, every 13-15 days, and most preferably, every 14 days.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions. In one embodiment, the invention provides a combination therapy for treating erosive polyarthritis comprising administering an anti-TNF antibody.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-TNFα antibody and another drug. The other drug(s) may be administered concomitant with, prior to, or following the administration of an anti-TNFα antibody.

The term "kit" as used herein refers to a packaged product or article of manufacture comprising components. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering the TNFα antibody, or antigen-binding portion thereof. In one embodiment the kit of the invention includes the formulation comprising the human antibody D2E7, as described in PCT/IB03/04502 and U.S. application Ser. No. 10/222,140, now abandoned.

Various aspects of the invention are described in further detail herein.

II. TNFα Inhibitors

This invention provides a method of treating erosive polyarthritis in which the administration of a TNFα inhibitor e.g., a TNFα antibody, or antigen-binding portion thereof, is beneficial. In one embodiment, these methods include administration of isolated human antibodies, or antigen-binding portions thereof, that bind to human TNFα with high affinity and a low off rate, and have a high neutralizing capacity. Preferably, the human antibodies of the invention are recombinant, neutralizing human anti-hTNFα antibodies.

In one embodiment, the TNFα inhibitor used in the invention is an anti-TNFα antibody, or a fragment thereof, including infliximab (REMICADE®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498,237; 6,451,983; and 6,448,380, each of which is incorporated by reference herein.

The most preferred recombinant, neutralizing antibody used in the invention is referred to herein as D2E7, also referred to as HUMIRA® and adalimumab (the amino acid sequence of the D2E7 VL region is shown in SEQ ID NO: 1; the amino acid sequence of the D2E7 VH region is shown in SEQ ID NO: 2). The properties of D2E7 (HUMIRA®) have been described in Salfeld et al., U.S. Pat. Nos. 6,090,382, 6,258,562, and 6,509,015, which are each incorporated by reference herein. Other examples of TNFα inhibitors include chimeric and humanized murine anti-hTNFα antibodies which have undergone clinical testing for treatment of rheumatoid arthritis (see e.g., Elliott et al. (1994) *Lancet* 344: 1125-1127; Elliot et al. (1994) *Lancet* 344:1105-1110; Rankin et al. (1995) *Br. J. Rheumatol.* 34:334–342). In another embodiment, the anti-TNFα antibody is multivalent.

In one embodiment, the method of treating erosive polyarthritis of the invention includes the administration of D2E7 antibodies and antibody portions, D2E7-related antibodies and antibody portions, and other human antibodies and antibody portions with equivalent properties to D2E7, such as high affinity binding to hTNFα with low dissociation kinetics and high neutralizing capacity. In one embodiment, the invention provides a method for treating erosive polyarthritis with an isolated human antibody, or an antigen-binding portion thereof, that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. More preferably, the isolated human antibody, or antigen-binding portion thereof, dissociates from human TNFα with a $K_{off}$ of $5\times10^{-4}$ s$^{-1}$ or less, or even more preferably, with a $K_{off}$ of $1\times10^{-4}$ s$^{-1}$ or less. More preferably, the isolated human antibody, or antigen-binding portion thereof, neutralizes human TNFα cytotoxicity in a standard in vitro L929 assay with an IC$_{50}$ of $1\times10^{-8}$ M or less, even more preferably with an IC$_{50}$ of $1\times10^{-9}$ M or less and still more preferably with an IC$_{50}$ of $1\times10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to methods of treating erosive polyarthritis by administering human antibodies that have slow dissociation kinetics for association with hTNFα and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the invention provides methods of treating erosive polyarthritis by the administration of an isolated human antibody, or antigen-binding portion thereof. The antibody or antigen-binding portion thereof preferably contains the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5 \times 10^{-4}$ s$^{-1}$ or less. Even more preferably, the antibody, or antigen-binding portion thereof, dissociates from human TNFα with a $K_{off}$ of $1 \times 10^{-4}$ s$^{-1}$ or less.

In yet another embodiment, the invention provides a method of treating erosive polyarthritis by administration of an isolated human antibody, or antigen-binding portion thereof. The antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_κI$ human germline family, more preferably from the A20 human germline Vk gene and most preferably from the D2E7 VL framework sequences shown in FIGS. 1A and 1B of U.S. Pat. No. 6,090,382. The framework regions for VH preferably are from the $V_H3$ human germline family, more preferably from the DP-31 human germline VH gene and most preferably from the D2E7 VH framework sequences shown in FIGS. 2A and 2B of U.S. Pat. No. 6,090,382.

Accordingly, in another embodiment, the invention provides a method of treating erosive polyarthritis by the administration of an isolated human antibody, or antigen-binding portion thereof. The antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention describes a method of treating erosive polyarthritis in which the administration of an anti-TNFα antibody wherein the antibody is an isolated human antibody, or an antigen-binding portion thereof. The antibody or antigen-binding portion thereof preferably contains D2E7-related VL and VH CDR3 domains, for example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the invention can also be modified. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (Cl—ClO) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat erosive polyarthritis and TNFα-related disorders of the invention by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield and Morrison (1991) *J. Exp. Med.* 173:1483-1491; and Lund et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel et al. (eds.) *Current Protocols in Molecular Biology*, Greene Publishing Associates, (1989) and in U.S. Pat. No. 4,816,397 by Boss et al.

To express D2E7 or a D2E7-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat et al. (1991) *Sequences of Proteins of Immunological Interest, Fifth Edition*, U.S. Department of Health and Human Services, NIH Publication No. 91-3242; Tomlinson et al. (1992) "The Repertoire of Human Germline $V_H$ Sequences Reveals about Fifty Groups of $V_H$ Segments with Different Hypervariable Loops" *J. Mol. Biol.* 227:776-798; and Cox et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in Kaufmnan and Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene *SurfZAP*™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VLNVH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human antibodies with high affinity and a low off rate constant for hTNFα are also described in U.S. Pat. Nos. 6,090,382, 6,258,562, and 6,509,015, each of which is incorporated by reference herein.

The TNFα inhibitor may also be a TNF fusion protein, e.g., etanercept (Enbrel®, Amgen; described in WO 91/03553 and WO 09/406476, incorporated by reference herein). In another embodiment, the TNFα inhibitor is a recombinant TNF binding protein (r-TBP-I) (Serono).

III. Treatment of Erosive Polyarthritis

The invention provides methods of treating erosive polyarthritis comprising administering a TNFα inhibitor, including, for an example, a TNFα antibody, to a subject having erosive polyarthritis. The invention also describes methods for determining the efficacy of a TNFα inhibitor for the treatment of erosive polyarthritis. Preferably, the TNFα is human TNFα and the subject is a human subject. In one embodiment, the TNFα inhibitor is adalimumab, also referred to as HUMIRA® or D2E7. The use of TNFα inhibitors, including antibodies and antibody portions, in the treatment of erosive polyarthritis, as well as methods for determining the efficacy of a TNFα inhibitor for the treatment of erosive polyarthritis, is discussed further below:

The term "polyarthritis" generally refers to inflammation, i.e., swelling, tenderness, or warmth, at two or more joints of a subject.

As used herein, the term "erosive polyarthritis" refers to a subject who has polyarthritis which is damaging to the joint.

The invention provides a method for treating erosive polyarthritis comprising administration of a TNFα inhibitor, including, for an example, a TNFα antibody. The invention also provides a method for inhibiting radiographic progression of joint disease associated with erosive polyarthritis. Methods for administering a TNFα antibody, or an antigen-binding portion thereof, for the treatment of erosive polyarthritis are described in more detail below.

The invention provides a method for determining the efficacy of an anti-TNFα treatment for erosive polyarthritis. Measures for determining such efficacy include tests which determine whether joint destruction or erosion is improved following treatment. For example, the Total Modified Sharp Score (mTSS) of a subject may be used to determine improvements in erosive polyarthritis in the subject. The mTSS may also be used as an assay to determine the efficacy of a treatment for erosive polyarthritis.

A Sharp score is an X-ray measurement in changes in total joint damage as assessed by bone erosions and joint space narrowing (Sharp et al. (1971) *Arthritis & Rheumatism* 14:706; Sharp et al. (1985) *Arthritis & Rheumatism* 28:16). The mTSS is a measure of the extent and severity of joint damage based on evaluations of x-rays of patients' hands and feet. Joints are scored for both joint erosions and joint space narrowing. The mTSS is the sum of the erosion score (ES) and the joint space narrowing (JSN) score and has, for example, a range of about 0 to about 398, where 0=no damage. The ES is the sum of joint scores collected for 46 joints and has a range, for example, of about 0 to about 230. The JSN is the sum of joint scores collected for 42 joints and has a range, for example, of about 0 to about 168. A score of 0 would indicate no change. In one embodiment of the invention, the mTSS is determined by combining the joint space narrowing score having a range of about 0-192 and an erosion score having a range of about 0-378.

An improved or constant mTSS demonstrates that the TNFα inhibitor is effective for treating erosive polyarthritis. In one embodiment, efficacy of a TNFα inhibitor for the treatment of erosive polyarthritis is evidenced by a lack of progression of joint disease, e.g., no change in Sharp score, in mTSS over time in a subject having erosive polyarthritis. In another embodiment, efficacy of a TNFα inhibitor for the treatment of erosive polyarthritis is evidenced by a decrease in the radiographic progression of joint disease, e.g., decrease in Sharp score, in mTSS over time in a subject having erosive polyarthritis.

In one embodiment, the overall change in the mTSS between baseline and a time period following treatment with a TNFα inhibitor is between about 0.9 and about −0.2. In another embodiment, the overall change in the mTSS between baseline and a time period following treatment with a TNFα inhibitor is between about 0.5 and about −0.2. In still another embodiment, the overall change in the mTSS between baseline and a time period following treatment with a TNFα inhibitor is between about 0.2 and about −0.2.

It should be noted that ranges intermediate to the above recited scores, e.g., about −0.1 to about 0.3, are also intended to be part of this invention. For example, ranges of values using a combination of any of the above recited values as upper and/or lower limits are intended to be included.

While treatment of an inflammatory disease with an anti-inflammatory agent may result in clinical improvements following treatment, there may still be progressive joint damage resulting from erosive polyarthritis (Gladman et al. (1990) *J Rheumatol* 17:809; Hanly et al. (1988) *Ann Rheum Dis* 47:386). Thus, it is a feature of this invention to provide a method for treating erosive polyarthritis which may be associated with another disorder. In a preferred embodiment, the invention includes treatment of erosive polyarthritis associated with a disorder in which TNFα activity is detrimental, including, but not limited to, rheumatoid arthritis (including juvenile rheumatoid arthritis), Crohn's disease, psoriasis, psoriatic arthritis, and ankylosing spondylitis. Erosive polyarthritis may also be associated with multicentric reticulohistiocytosis (MRH) (Santilli et al. (2002) *Ann Rehum Dis* 61: 485).

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above. There are numerous examples of disorders in which TNFα activity is detrimental. The use of TNFα inhibitors for the treatment of erosive polyarthritis associated with specific disorders is discussed further below:

A. Autoimmune Diseases

In one embodiment, the invention includes treatment of erosive polyarthritis associated with an autoimmune disease. Erosive polyarthritis may be found in patients suffering from autoimmune diseases, including forms of arthritis such as rheumatoid arthritis and juvenile rheumatoid arthritis (Verloes (1998) *Med Genet.* 35:943). TNFα antibodies, such as adalimumab, may be used to treat autoimmune diseases, in particular those associated with erosive polyarthritis. Examples of such autoimmune conditions include rheumatoid arthritis, rheumatoid spondylitis, osteoarthritis and gouty arthritis, allergy, multiple sclerosis, autoimmune diabetes, autoimmune uveitis and nephrotic syndrome. Other examples of autoimmune conditions include multisystem autoimmune diseases and autoimmune hearing loss. Other examples of autoimmune disease are described in U.S. application Ser. No. 10/622,932, incorporated by reference herein.

Juvenile Rheumatoid Arthritis

Tumor necrosis factor has been implicated in the pathophysiology of juvenile arthritis, including juvenile rheumatoid arthritis (Grom et al. (1996) *Arthritis Rheum.* 39:1703; Mangge et al. (1995) *Arthritis Rheum.* 8:211). In one embodiment, the TNFα antibody of the invention is used to treat juvenile rheumatoid arthritis.

The term "juvenile rheumatoid arthritis" or "JRA" as used herein refers to a chronic, inflammatory disease which occurs before age 16 that may cause joint or connective tissue damage. JRA is also referred to as juvenile chronic polyarthritis and Still's disease.

JRA causes joint inflammation and stiffness for more than 6 weeks in a child of 16 years of age or less. Inflammation causes redness, swelling, warmth, and soreness in the joints. Any joint can be affected and inflammation may limit the mobility of affected joints. One type of JRA can also affect the internal organs.

JRA is often classified into three types by the number of joints involved, the symptoms, and the presence or absence of certain antibodies found by a blood test. These classifications help the physician determine how the disease will progress and whether the internal organs or skin is affected. The classifications of JRA include the following:

a. Pauciarticular JRA, wherein the patient has four or fewer joints are affected. Pauciarticular is the most common form of JRA, and typically affects large joints, such as the knees.

b. Polyarticular HRA, wherein five or more joints are affected. The small joints, such as those in the hands and feet, are most commonly involved, but the disease may also affect large joints.

c. Systemic JRA is characterized by joint swelling, fever, a light skin rash, and may also affect internal organs such as the heart, liver, spleen, and lymph nodes. Systemic JRA is also referred to as it Still's disease. A small percentage of these children develop arthritis in many joints and can have severe arthritis that continues into adulthood.

B. Spondyloarthropathies

In one embodiment, the invention includes treatment of erosive polyarthritis associated with a spondylarthopathy. Erosive polyarthritis may be found in patients suffering from inflammatory diseases, such as spondyloarthopathies, associated with detrimental TNFα activity (see e.g., Moeller et al. (1990) *Cytokine* 2:162; U.S. Pat. No. 5,231,024; European Patent Publication No. 260 610).

As used herein, the term "spondyloarthropathy" or "spondyloarthropathies" is used to refer to any one of several diseases affecting the joints of the spine, wherein such diseases share common clinical, radiological, and histological features. A number of spondyloarthropathies share genetic characteristics, i.e. they are associated with the HLA-B27 allele. In one embodiment, the term spondyloarthropathy is used to refer to any one of several diseases affecting the joints of the spine, excluding ankylosing spondylitis, wherein such diseases share common clinical, radiological, and histological features. Examples of spondyloarthropathies include ankylosing spondylitis, psoriatic arthritis/spondylitis, enteropathic arthritis, reactive arthritis or Reiter's syndrome, and undifferentiated spondyloarthropathies. Examples of animal models used to study spondyloarthropathies include ank/ank transgenic mice, HLA-B27 transgenic rats (see Taurog et al. (1998) *The Spondylarthritides*. Oxford:Oxford University Press).

Examples of subjects who are at risk of having spondyloarthropathies include humans suffering from arthritis. Spondyloarthropathies can be associated with forms of arthritis, including rheumatoid arthritis. In one embodiment of the invention, a TNFα inhibitor is used to treat a subject who suffers from a spondyloarthropathy associated with erosive polyarthritis. Examples of spondyloarthropathies which can be treated with a TNFα inhibitor are described below:

Ankylosing Spondylitis (AS)

In one embodiment, the invention includes treatment of erosive polyarthritis associated with ankylosing spondylitis using a TNFα antibody, or antigen-binding portion thereof. Tumor necrosis factor has been implicated in the pathophysiology of ankylosing spondylitis (see Verjans et al. (1991) *Arthritis Rheum.* 34:486; Verjans et al. (1994) *Clin Exp Immunol.* 97:45; Kaijtzel et al. (1999) *Hum Immunol.* 60:140). Ankylosing spondylitis (AS) is an inflammatory disorder involving inflammation of one or more vertebrae. AS is a chronic inflammatory disease that affects the axial skeleton and/or peripheral joints, including joints between the vertebrae of the spine and sacroiliac joints and the joints between the spine and the pelvis. AS can eventually cause the affected vertebrae to fuse or grow together. Spondyarthropathies, including AS, can be associated with psoriatic arthritis (PsA) and/or inflammatory bowel disease (IBD), including ulcerative colitis and Crohn's disease.

Early manifestations of AS can be determined by radiographic tests, including CT scans and MRI scans. Early manifestations of AS often include scroiliitis and changes in the sacroliac joints as evidenced by the blurring of the cortical margins of the subchrondral bone, followed by erosions and sclerosis. Fatigue has also been noted as a common symptom of AS (Duffy et al. (2002) *ACR 66th Annual Scientific Meeting Abstract*).

Psoriatic Arthritis

In one embodiment, the invention includes treatment of erosive polyarthritis associated with psoriatic arthritis using a TNFα antibody, or antigen-binding portion thereof. Tumor necrosis factor has been implicated in the pathophysiology of psoriatic arthritis (PsA) (Partsch et al. (1998) *Ann Rheum Dis.* 57:691; Ritchlin et al. (1998) *J Rheumatol.* 25:1544). As referred to herein, psoriatic TNFα has been implicated in activating tissue inflammation and causing joint destruction in rheumatoid arthritis (see e.g., Moeller, A., et al. (1990) *Cytokine* 2:162-169; U.S. Pat. No. 5,231,024 to Moeller et al.; European Patent Publication No. 260 610 B1 by Moeller, A.; Tracey and Cerami, supra; Arend, W. P. and Dayer, J-M. (1995) *Arth. Rheum.* 38:151-160; Fava, R. A., et al. (1993) *Clin. Exp. Immunol.* 94:261-266). TNFα also has been implicated in promoting the death of islet cells and in mediating insulin resistance in diabetes (see e.g., Tracey and Cerami, supra; PCT Publication No. WO 94/08609). TNFα also has been implicated in mediating cytotoxicity to oligodendrocytes and induction of inflammatory plaques in multiple sclerosis (see e.g., Tracey and Cerami, supra). Chimeric and humanized murine anti-hTNFα antibodies have undergone clinical testing for treatment of rheumatoid arthritis (see e.g., Elliott, M. J., et al. (1994) *Lancet* 344:1125-1127; Elliot, M. J., et al. (1994) *Lancet* 344:1105-1110; Rankin, E. C., et al. (1995) *Br. J. Rheumatol.* 34:334-342).

Psoriatic arthritis refers to chronic inflammatory arthritis which is associated with psoriasis, a common chronic skin condition that causes red patches on the body. About 1 in 20 individuals with psoriasis will develop arthritis along with the skin condition, and in about 75% of cases, psoriasis precedes the arthritis. PsA exhibits itself in a variety of ways, ranging from mild to severe arthritis, wherein the arthritis usually affects the fingers and the spine. When the spine is affected, the symptoms are similar to those of ankylosing spondylitis, as described above. A TNFα antibody, or antigen-binding fragment thereof, can be used for treatment of erosive polyarthritis associated with PsA.

PsA is sometimes associated with arthritis mutilans. Arthritis mutilans refers to a disorder which is characterized by excessive bone erosion resulting in a gross, erosive deformity which mutilates the joint.

Characteristic radiographic features of PsA include joint erosions, joint space narrowing, bony proliferation including periarticular and shaft periostitis, osteolysis including "pencil in cup" deformity and acro-osteolysis, ankylosis, spur formation, and spondylitis (Wassenberg et al. (2001) *Z Rheumatol* 60:156). Unlike rheumatoid arthritis (RA), joint involvement in PsA is often asymmetrical and may be oligoarticular;

osteoporosis is atypical. Although erosive changes in early PsA are marginal as in RA, they become irregular and ill defined with disease progression because of periosteal bone formation adjacent to the erosions. In severe cases, erosive changes may progress to development of pencil in cup deformity or gross osteolysis (Gold et al. (1988) *Radiol Clin North Am* 26:1195; Resnick et al. (1977)) *J Can Assoc Radiol* 28:187). Asymmetrical erosions may be visible radiographically in the carpus and in the metacarpophalangeal (MCP), proximal interphalangeal (PIP), and distal interphalangeal (DIP) joints of the hands, but the DIP joints are often the first to be affected. Abnormalities are seen in the phalangeal tufts and at the sites of attachments of tendons and ligaments to the bone. The presence of DIP erosive changes may provide both sensitive and specific radiographic findings to support the diagnosis of PsA. Also, the hands tend to be involved much more frequently than the feet with a ratio of nearly 2:1.

Other examples of spondyloarthropathies are described in U.S. application Ser. No. 10/622,932, incorporated by reference herein.

C. Skin and Nail Disorders

In one embodiment, the invention includes treatment of erosive polyarthritis associated with skin and nail disorders. As used herein, the term "skin and nail disorder in which TNFα activity is detrimental" is intended to include skin and/or nail disorders and other disorders in which the presence of TNFα in a subject suffering from the disorder has been shown to be or is suspected of being either responsible for the pathophysiology of the disorder or a factor that contributes to a worsening of the disorder, e.g., psoriasis. Accordingly, skin and nail disorders in which TNFα activity is detrimental are disorders in which inhibition of TNFα activity is expected to alleviate the symptoms and/or progression of the disorder. The use of the antibodies, antibody portions, and other TNFα inhibitors for the treatment of specific skin and nail disorders is discussed further below. In certain embodiments, the antibody, antibody portion, or other TNFα inhibitor of the invention is administered to the subject in combination with another therapeutic agent, as described below. In one embodiment, a TNFα antibody is administered to the subject in combination with another therapeutic agent for the treatment of erosive polyarthritis associated with psoriasis and the treatment of psoriasis associated with arthritis.

Psoriasis

Tumor necrosis factor has been implicated in the pathophysiology of psoriasis (Takematsu et al. (1989) *Arch Dermatol Res.* 281:398; Victor and Gottlieb (2002) *J Drugs Dermatol.* 1(3):264). Psoriasis is described as a skin inflammation (irritation and redness) characterized by frequent episodes of redness, itching, and thick, dry, silvery scales on the skin. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the epidermis and polymorphonuclear leukocyte and lymphocyte infiltration into the epidermis layer resulting in an increase in the basal cell cycle. Psoriasis often involves the nails, which frequently exhibit pitting, separation of the nail, thickening, and discoloration. Psoriasis is often associated with other inflammatory disorders, for example arthritis, including rheumatoid arthritis, inflammatory bowel disease (IBD), and Crohn's disease.

Evidence of psoriasis is most commonly seen on the trunk, elbows, knees, scalp, skin folds, or fingernails, but it may affect any or all parts of the skin. Normally, it takes about a month for new skin cells to move up from the lower layers to the surface. In psoriasis, this process takes only a few days, resulting in a build-up of dead skin cells and formation of thick scales. Symptoms of psoriasis include: skin patches, that are dry or red, covered with silvery scales, raised patches of skin, accompanied by red borders, that may crack and become painful, and that are usually lovated on the elbows, knees, trunk, scalp, and hands; skin lesions, including pustules, cracking of the skin, and skin redness; joint pain or aching which may be associated with of arthritis, e.g., psoriatic arthritis.

Treatment for psoriasis often includes a topical corticosteroids, vitamin D analogs, and topical or oral retinoids, or combinations thereof. In one embodiment, the TNFα inhibitor of the invention is administered in combination with or the presence of one of these common treatments. Additional therapeutic agents which can also be combined with the TNFα inhibitor for treatment of psoriasis are described in more detail below.

The diagnosis of psoriasis is usually based on the appearance of the skin. Additionally a skin biopsy, or scraping and culture of skin patches may be needed to rule out other skin disorders. An x-ray may be used to check for psoriatic arthritis if joint pain is present and persistent.

In one embodiment of the invention, a TNFα inhibitor is used to treat psoriasis, including chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). Specific types of psoriasis included in the treatment methods of the invention include chronic plaque psoriasis, guttate psoriasis, inverse psoriasis, and pustular psoriasis. Other examples of psoriasis and other types of skin and nail disorders are described in U.S. application Ser. No. 10/622,932, incorporated by reference herein.

Methods for determining the efficacy of a TNFα inhibitor for the treatment of erosive polyarthritis in association a disorder in which TNFα activity is detrimental include any assay which measures the degree of joint destruction, including joint space narrowing and/or joint erosion. In one embodiment, joint destruction is measured using radiography. Such assays may be used to examine the efficacy of the TNFα inhibitor by determining whether an improvement occurs in a subject or patient population treated with the TNFα inhibitor. Generally, improvements are determined by comparing a baseline score determined prior to treatment, and a score determined at a time following treatment with the TNFα inhibitor.

Additional improvements in arthritic conditions, such as Ra, PsA, and JRA, may be determined by measuring the ACR response. ACR thresholds, e.g., ACR20, ACR50, ACR70, may be used for defining improvement in RA and PsA, and indicate the percentage improvement in seven disease activity measures. Criteria include percentage improvement in tender and swollen joint count and improvement of at least 3 of the following criteria: patient pain assessment, patient global assessment, physician global assessment, patient self-assessed disability, or laboratory measures of disease activity (i.e., erythrocyte sedimentation rate or C-reactive protein level) (Felson et al. (1993) *Arthritis Rheum.* 36(6):729).

Other assays used to determine improvement for a given therapy for the treatment of RA, JRA, and PsA, include the EULAR response, DAS score, FACIT-F, HAQ score, and SJC and/or TJC counts.

The EULAR criteria uses a DAS for defining response. Response is defined as both: (a) change in disease activity from baseline and (b) the level of disease activity reached during follow-up. Criteria used to define DAS include: Ritchie articular index, swollen joint count (44-joint count), erythrocyte sedimentation rate, and Health Assessment Questionnaire. A modified version of the DAS criteria, DAS28, uses a 28-joint count for swollen and tender joints. Response is defined as a combination of a significant change from baseline and the level of disease activity attained. Good response is defined as a significant decrease in DAS (>1.2) and a low level of disease activity (< or =2.4). Non-response is defined as a decrease < or =0.6, or a decrease >0.6 and < or =1.2 with an attained DAS >3.7. Any other scores are regarded as moderate responses.

The DAS is a score is based on the Ritchie articular index, a 44 swollen joint count, ESR, and a general health assessment on a VAS. Range varies from 1 to 9. Serial measurements of the DAS and DAS28 are strong predictors of physical disability and radiological progression, and both indices are sensitive discriminators between patients with high and low disease activity and between active and placebo treated patient groups.

FACIT-F (Functional Assessment of Chronic Illness Therapy-Fatigue) is a validated questionnaire designed to measure patients' assessment of fatigue-related factors in chronic illness (see Cella and Webster (1997) *Oncology (Huntingt)*. 11:232 and Lai et al. (2003) *Qual Life Res*. 12(5):485).

The Health Assessment Questionnaire (HAQ) is a validated questionnaire designed to assess patients' ability to perform activities of daily living, particularly in adult arthritics. Instrument consists of the HAQ Disability Index (20 items), Pain Scale (1 item), and Global Health Status (1 item) that measure disability/physical functioning and quality of life (Fries et al. (1982) *J Rheumatol*. 9(5):789).

Swollen and tender joints (SJC and TJC) are the most characteristic features of RA, and disease severity is directly related to the number of swollen and tender joints. Counting swollen and tender joints is a key component of the clinical assessment of RA.

Improvements in PsA and psoriasis may also be determined using the PASI response, DLQI, and the BSA score. DLQI (Dermatology Life Quality Index) is a health-related quality of life measure widely used for a variety of dermatological diseases, including PsA and psoriasis. The body Surface Area (BSA) score provides a measurement of surface area based on height and weight and expressed in $m^2$. The PASI (Psoriasis Area and Severity Index) is a composite measure of the erythema, induration, desquamation and body surface area that is affected by psoriasis for a particular patient. Patients are evaluated for head, trunk, upper and lower limb involvement. Scores range from 0 (clear) to 72 (maximum severity).

Improvements in treatment for PsA may also be measured using the PsARC (Psoriatic Arthritis Response Criteria), which provides a clinical measure of the change in tender and swollen joint scores, along with a series of global assessments of disease activity.

Improvements in AS may be measured by using any number of instruments to evaluate various AS symptoms. Some of the commonly used scales include the Assessment in Ankylosing Spondylitis (ASAS), the Bath Ankylosing Spondylitis Disease Activity Index (BASDAI) (Garrett et al. (1994) *J Rheumatol* 21:2286), the Bath Ankylosing Spondylitis Metrology Index (BASMI) (Jenkinson et al. (1994) *J Rheumatol* 21:1694), and the Bath Ankylosing Spondylitis Functional Index (BASFI) (Calin et al. (1994) *J Rheumatol* 21:2281). These indices can be used to monitor a patient over time and to determine improvement. Additional description measurements for assessing improvements in AS are described in U.S. application Ser. No. 10/622,932, incorporated by reference herein.

IV. Pharmaceutical Compositions and Pharmaceutical Administration

A. Compositions and Administration

Antibodies, antibody-portions, and other TNFα inhibitors for use in the methods of the invention, may be incorporated into pharmaceutical compositions suitable for administration to a subject having erosive polyarthritis. Typically, the pharmaceutical composition comprises an antibody, antibody portion, or other TNFα inhibitor of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In one embodiment, the antibody or other TNFα inhibitor is administered by intravenous infusion or injection. In another embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Supplementary active compounds can also be incorporated into the compositions. In certain embodiments, an antibody or antibody portion for use in the methods of the invention is coformulated with and/or coadministered with one or more additional therapeutic agents, including an erosive polyarthritis inhibitor or antagonist. For example, an anti-hTNFα antibody or antibody portion of the invention may be coformulated and/or coadministered with one or more additional antibodies that bind other targets associated with erosive polyarthritis (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

In one embodiment, the invention includes pharmaceutical compositions comprising an effective amount of a TNFα inhibitor and a pharmaceutically acceptable carrier, wherein the effective amount of the TNFα inhibitor may be effective to treat erosive polyarthritis. In one embodiment, the antibody or antibody portion for use in the methods of the invention is incorporated into a pharmaceutical formulation as described in PCT/IB03/04502 and U.S. application Ser. No. 10/222,140, now abandoned, incorporated by reference herein. This formulation includes a concentration 50 mg/ml of the antibody D2E7, wherein one pre-filled syringe contains 40 mg of antibody for subcutaneous injection. In another embodiment, the formulation of the invention includes D2E7.

The antibodies, antibody-portions, and other TNFα inhibitors of the present invention can be administered by a variety of methods known in the art, although for many therapeutic applications, the preferred route/mode of administration is subcutaneous injection. In another embodiment, administration is via intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Dekker, Inc., New York, 1978.

TNFα antibodies may also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. application Ser. No. 10/222,140, now abandoned, incorporated by reference herein, are used to treat erosive polyarthritis using treatment methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

In one embodiment, the invention provides a single dose method for treating erosive polyarthritis, comprising administering to a subject in need thereof a single dose of a TNFα inhibitor, such as a human antibody. In one embodiment, the TNFα inhibitor is the anti-TNFα antibody adalimumab. The single dose of TNFα inhibitor can be any therapeutically or prophylactically effective amount. In one embodiment, a subject is administered either a 20 mg, a 40 mg, or an 80 mg single dose of adalimumab (also referred to as D2E7). The single dose may be administered through any route, including, for example, subcutaneous administration. Biweekly dosing regimens can be used to treat erosive polyarthritis and are further described in U.S. application Ser. No. 10/163,657. Multiple variable dose methods of treatment or prevention can also be used to treat erosive polyarthritis, and are further described in PCT appln. no. PCT/US05/012007.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. It should also be noted that the invention pertains to methods of treatment of erosive polyarthritis including acute management and chronic management of the disease.

The invention also pertains to packaged pharmaceutical compositions or kits for administering the anti-TNF antibodies of the invention for the treatment of erosive polyarthritis. In one embodiment of the invention, the kit comprises a TNFα inhibitor, such as an antibody, a second pharmaceutical composition comprising an additional therapeutic agent, and instructions for administration for treatment of erosive polyarthritis. The instructions may describe how, e.g., subcutaneously, and when, e.g., at week 0 and week 2, the different doses of TNFα inhibitor and/or the additional therapeutic agent shall be administered to a subject for treatment.

Another aspect of the invention pertains to kits containing a pharmaceutical composition comprising an anti-TNFα antibody and a pharmaceutically acceptable carrier and one or more pharmaceutical compositions each comprising a drug useful for treating erosive polyarthritis and a pharmaceutically acceptable carrier. Alternatively, the kit comprises a single pharmaceutical composition comprising an anti-TNFα antibody, one or more drugs useful for treating erosive polyarthritis and a pharmaceutically acceptable carrier. The kits contain instructions for dosing of the pharmaceutical compositions for the treatment of erosive polyarthritis.

The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

B. Additional Therapeutic Agents

The invention also describes methods of treating erosive polyarthritis comprising administering a TNFα inhibitor in combination with an additional therapeutic agent. The invention also pertains to pharmaceutical compositions and methods of use thereof for the treatment of erosive polyarthritis in combination with an additional therapeutic agent. The pharmaceutical compositions comprise a first agent that treats erosive polyarthritis. The pharmaceutical composition also may comprise a second agent that is an active pharmaceutical ingredient; that is, the second agent is therapeutic and its function is beyond that of an inactive ingredient, such as a pharmaceutical carrier, preservative, diluent, or buffer. In one embodiment, the second agent may be useful in treating or preventing erosive polyarthritis. In another embodiment, the second agent may diminish or treat at least one symptom(s) associated with the disorder which is associated with erosive polyarthritis, e.g., psoriatic arthritis. In yet another embodiment, the additional agent is useful for the treatment of both erosive polyarthritis and the additional disorder. The first and second agents may exert their biological effects by similar or unrelated mechanisms of action; or either one or both of the first and second agents may exert their biological effects by a multiplicity of mechanisms of action. A pharmaceutical composition may also comprise a third compound, or even more yet, wherein the third (and fourth, etc.) compound has the same characteristics of a second agent.

It should be understood that the pharmaceutical compositions described herein may have the first and second, third, or additional agents in the same pharmaceutically acceptable carrier or in a different pharmaceutically acceptable carrier for each described embodiment. It further should be understood that the first, second, third and additional agent may be administered simultaneously or sequentially within described embodiments. Alternatively, a first and second agent may be administered simultaneously, and a third or additional agent may be administered before or after the first two agents.

The combination of agents used within the methods and pharmaceutical compositions described herein may have a therapeutic additive or synergistic effect on the condition(s) or disease(s) targeted for treatment. The combination of agents used within the methods or pharmaceutical compositions described herein also may reduce a detrimental effect associated with at least one of the agents when administered alone or without the other agent(s) of the particular pharmaceutical composition. For example, the toxicity of side effects of one agent may be attenuated by another agent of the composition, thus allowing a higher dosage, improving patient compliance, and improving therapeutic outcome. The additive or synergistic effects, benefits, and advantages of the compositions apply to classes of therapeutic agents, either structural or functional classes, or to individual compounds themselves.

Supplementary active compounds can also be incorporated into the compositions. In certain embodiments, an antibody or antibody portion of the invention is coformulated with and/or coadministered with one or more additional therapeutic agents that are useful for treating erosive polyarthritis. For example, an anti-hTNFα antibody, antibody portion, or other TNFα inhibitor of the invention may be coformulated and/or coadministered with one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751). Furthermore, one or more antibodies or other TNFα inhibitors of the invention may be used in combination with two or more of the foregoing therapeutic agents. Such combination therapies may advantageously utilize lower dosages of the administered therapeutic agents, thus avoiding possible toxicities or complications associated with the various monotherapies.

TNFα inhibitors, e.g., a TNFα antibody, or antigen-binding portion thereof, described herein may be used in combination with additional therapeutic agents for the treatment erosive polyarthritis. Preferably the other drug is a Disease Modifying Anti-Rheumatic Drug (DMARD) or a Nonsteroidal Antiinflammatory Drug (NSAID) or a steroid or any combination thereof. Preferred examples of a DMARD are hydroxychloroquine, leflunomide, methotrexate, parenteral gold, oral gold and sulfasalazine.

Nonlimiting additional agents which can also be used in combination with a TNFα inhibitor, e.g., a TNFα antibody, or antigen-binding portion thereof, to treat erosive polyarthritis include, but are not limited to, the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; see e.g., *Arthritis & Rheumatism* (1994) Vol. 37, S295; *J. Invest. Med.* (1996) Vol. 44, 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., *Arthritis & Rheumatism* (1996) Vol. 39, No. 9 (supplement), S284; *Amer. J. Physiol.—Heart and Circulatory Physiology* (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g., *Arthritis & Rheumatism* (1996) Vol. 39, No. 9 (supplement), S81); Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), S282) and thalidomide-related drugs (e.g., Celgen); leflunomide (anti-inflammatory and cytokine inhibitor; see e.g., *Arthritis & Rheumatism* (1996) Vol. 39, No. 9 (supplement), S131; *Inflammation Research* (1996) Vol. 45, pp. 103-107); tranexamic acid (inhibitor of plasminogen activation; see e.g., *Arthritis & Rheumatism* (1996) Vol. 39, No. 9 (supplement), S284); T-614 (cytokine inhibitor; see e.g., *Arthritis & Rheumatism* (1996) Vol. 39, No. 9 (supplement), S282); prostaglandin E1 (see e.g., *Arthritis & Rheumatism* (1996) Vol. 39, No. 9 (supplement), S282); Tenidap (non-steroidal anti-inflammatory drug; see e.g., *Arthritis & Rheumatism* (1996) Vol. 39, No. 9 (supplement), S280); Naproxen (non-steroidal anti-inflammatory drug; see e.g., *Neuro Report* (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., *Arthritis & Rheumatism* (1996) Vol. 39, No. 9 (supplement), S281); Azathioprine (see e.g., *Arthritis & Rheumatism* (1996) Vol. 39, No. 9 (supplement), S281); ICE inhibitor (inhibitor of the enzyme interleukin-1β, converting enzyme); zap-70 and/or lck inhibitor (inhibitor of the tyrosine kinase zap-70 or lck); VEGF inhibitor and/or VEGF-R inhibitor (inhibitos of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin-17 inhibitors (see e.g., *Arthritis & Rheumatism* (1996) Vol. 39, No. 9 (supplement), S120); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents. Any of the above-mentioned agents can be administered in combination with the TNFα inhibitor, including a TNFα antibody, to treat erosive polyarthritis or to inhibit radiographic progression of joint disease.

In one embodiment, the TNFα inhibitor, e.g. a TNFα antibody, or antigen-binding portion thereof, is administered in combination with one of the following agents for the treatment of rheumatoid arthritis: small molecule inhibitor of KDR (ABT-123), small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline hcl; sulfadiazine; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; ABT-874; ABT-325 (anti-IL 18); anti-IL 15; BIRB-796; SCIO-469; VX-702; AMG-548; VX-740; Roflumilast; IC-485; CDC-801; and mesopram. In another embodiment, the TNFα antibody of the invention is administered for the treatment of a TNFα related disorder in combination with one of the above mentioned agents for the treatment of rheumatoid arthritis.

In one embodiment, the TNFα inhibitor, e.g., a TNFα antibody, or antigen-binding portion thereof, is used in combination with a drug used to treat Crohn's disease or a Crohn's-related disorder. Examples of therapeutic agents which can be used to treat Crohn's include mesalamine, prednisone, azathioprine, mercaptopurine, infliximab, budesonide, sulfasalazine, methylprednisolone sod succ, diphenoxylate/atrop sulf, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab, and interferon-gamma.

In one embodiment, the TNFα inhibitor, e.g., a TNFα antibody, or antigen-binding portion thereof, is administered in combination with an agent which is commonly used to treat spondyloarthropathies, such as AS. Examples of such agents include nonsteroidal, anti-inflammatory drugs (NSAIDs), COX 2 inhibitors, including Celebrex®, Vioxx®, and Bextra®, and etoricoxib. Physiotherapy is also commonly used to treat spondyloarthropathies, usually in conjunction with nonsteoidal inflammatory drugs.

In one embodiment, the TNFα inhibitor, e.g., a TNFα antibody, or antigen-binding portion thereof, is administered in combination with an additional therapeutic agent to treat ankylosing spondylitis. Examples of agents which can be used to reduce or inhibit the symptoms of ankylosing spondylitis include ibuprofen, diclofenac and misoprostol, naproxen, meloxicam, indomethacin, diclofenac, celecoxib, rofecoxib, sulfasalazine, prednisone, methotrexate, azathioprine, minocyclin, prednisone, etanercept, and infliximab.

In one embodiment, the TNFα inhibitor, e.g., a TNFα antibody, or antigen-binding portion thereof, is administered in combination with an additional therapeutic agent to treat psoriatic arthritis. Examples of agents which can be used to reduce or inhibit the symptoms of psoriatic arthritis include methotrexate; etanercept; rofecoxib; celecoxib; folic acid; sulfasalazine; naproxen; leflunomide; methylprednisolone acetate; indomethacin; hydroxychloroquine sulfate; sulindac; prednisone; betamethasone diprop augmented; infliximab; methotrexate; folate; triamcinolone acetonide; diclofenac; dimethylsulfoxide; piroxicam; diclofenac sodium; ketoprofen; meloxicam; prednisone; methylprednisolone; nabumetone; tolmetin sodium; calcipotriene; cyclosporine; diclofenac; sodium/misoprostol; fluocinonide; glucosamine sulfate; gold sodium thiomalate; hydrocodone; bitartrate/apap; ibuprofen; risedronate sodium; sulfadiazine; thioguanine; valdecoxib; alefacept; and efalizumab.

In one embodiment, the TNFα inhibitor, e.g., a TNFα antibody, or antigen-binding portion thereof, is administered in combination with topical corticosteroids, vitamin D analogs, and topical or oral retinoids, or combinations thereof, for the treatment of psoriasis. In addition, the TNFα antibody of the invention is administered in combination with one of the following agents for the treatment of psoriasis: small molecule inhibitor of KDR (ABT-123), small molecule inhibitor of Tie-2, calcipotriene, clobetasol propionate, triamcinolone acetonide, halobetasol propionate, tazarotene, methotrexate, fluocinonide, betamethasone diprop augmented, fluocinolone, acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, coal tar, diflorasone diacetate, etanercept, folate, lactic acid, methoxsalen, hc/bismuth subgal/znox/resor, methylprednisolone acetate, prednisone, sunscreen, salicylic acid, halcinonide, anthralin, clocortolone pivalate, coal extract, coal tar/salicylic acid, coal tar/salicylic acid/sulfur, desoximetasone, diazepam, emollient, pimecrolimus emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, alefacept, efalizumab, tacrolimus, pimecrolimus, PUVA, UVB, and sulfasalazine.

An antibody, antibody portion, or other TNFα inhibitor, e.g., a TNFα antibody, or antigen-binding portion thereof, may be used in combination with other agents to treat skin conditions. For example, an antibody, antibody portion, or other TNFα inhibitor of the invention is combined with PUVA therapy. PUVA is a combination of psoralen (P) and long-wave ultraviolet radiation (UVA) that is used to treat many different skin conditions. The antibodies, antibody portions, or other TNFα inhibitors of the invention can also be combined with pimecrolimus. In another embodiment, the antibodies of the invention are used to treat psoriasis, wherein the antibodies are administered in combination with tacrolimus. In a further embodiment, tacrolimus and TNFα inhibitors are administered in combination with methotrexate and/or cyclosporine. In still another embodiment, the TNFα inhibitor of the invention is administered with excimer laser treatment for treating psoriasis.

Nonlimiting examples of other therapeutic agents with which a TNFα inhibitor, e.g., a TNFα antibody, or antigen-binding portion thereof, can be combined to treat a skin or nail disorder include UVA and UVB phototherapy. Other nonlimiting examples which can be used in combination with a TNFα inhibitor include anti-IL-12 and anti-IL-18 therapeutic agents, including antibodies.

Any one of the above-mentioned therapeutic agents, alone or in combination therewith, can be administered to a subject suffering from erosive polyarthritis, in combination with the TNFα α inhibitor, including a TNFα antibody, or antigen-binding portion thereof. A TNFα antibody, or antigen-binding portion thereof, may be used in combination with additional therapeutic agents known to be effective at acute management of subjects with erosive polyarthritis. A TNFα antibody, or antigen-binding portion thereof, may also be used in combination with additional therapeutic agents known to be effective at management of subjects with erosive polyarthritis.

This invention is further illustrated by the following example which should not be construed as limiting. The contents of all references, patents and published patent applications cited throughout this application are incorporated herein by reference.

EXAMPLE

Treatment of Erosive Polyarthritis in Patients with Psoriatic Arthritis Using a TNF Inhibitor Erosive polyarthritis occurs in a substantial proportion of patients with psoriatic arthritis (PsA). Traditional, non-biologic DMARDs have not been shown to effectively inhibit the radiographic progression of joint damage in this disease.

The following study was performed to evaluate the efficacy of a TNF inhibitor, more specifically the anti-TNF antibody adalimumab, for the treatment of erosive polyarthritis. The study was performed to evaluate whether adalimumab was effective at inhibiting the radiographic progression of joint disease associated with erosive polyarthritis in patients with moderate to severe PsA.

A 24-week, double-blind, randomized, placebo-controlled trial of adult patients with moderate to severely active PsA (≥3 swollen and ≥3 tenderjoints) who had failed NSAID therapy was performed. Patients were stratified according to methotrexate (MTX) use (yes/no) and degree of psoriasis (<3% or ≥3% Body Surface Area [BSA]). In addition to having ≥3 swollen and ≥3 tender joints, inclusion criteria included an inadequate response to NSAID therapy, a history of psoriasis, and age ≥18 years. Exclusion criteria included the following: prior anti-TNF therapy, alefacept within 12 weeks prior to study entry, other biologics within 6 weeks prior to study entry, systemic therapies for psoriasis within 4 weeks prior to study entry, and phototherapy and topicals within 2 weeks prior to study entry.

Patients were randomized to receive either adalimumab 40 mg or placebo subcutaneously every other week (eow) for 24 weeks. Patients who completed the 24-week trial were eligible to enroll in an open-label extension (OLE) study, in which all patients received adalimumab eow. After 12 weeks of treatment with open label therapy, patients failing to meet pre-specified criteria were eligible to receive 40 mg weekly.

Figure 1B:
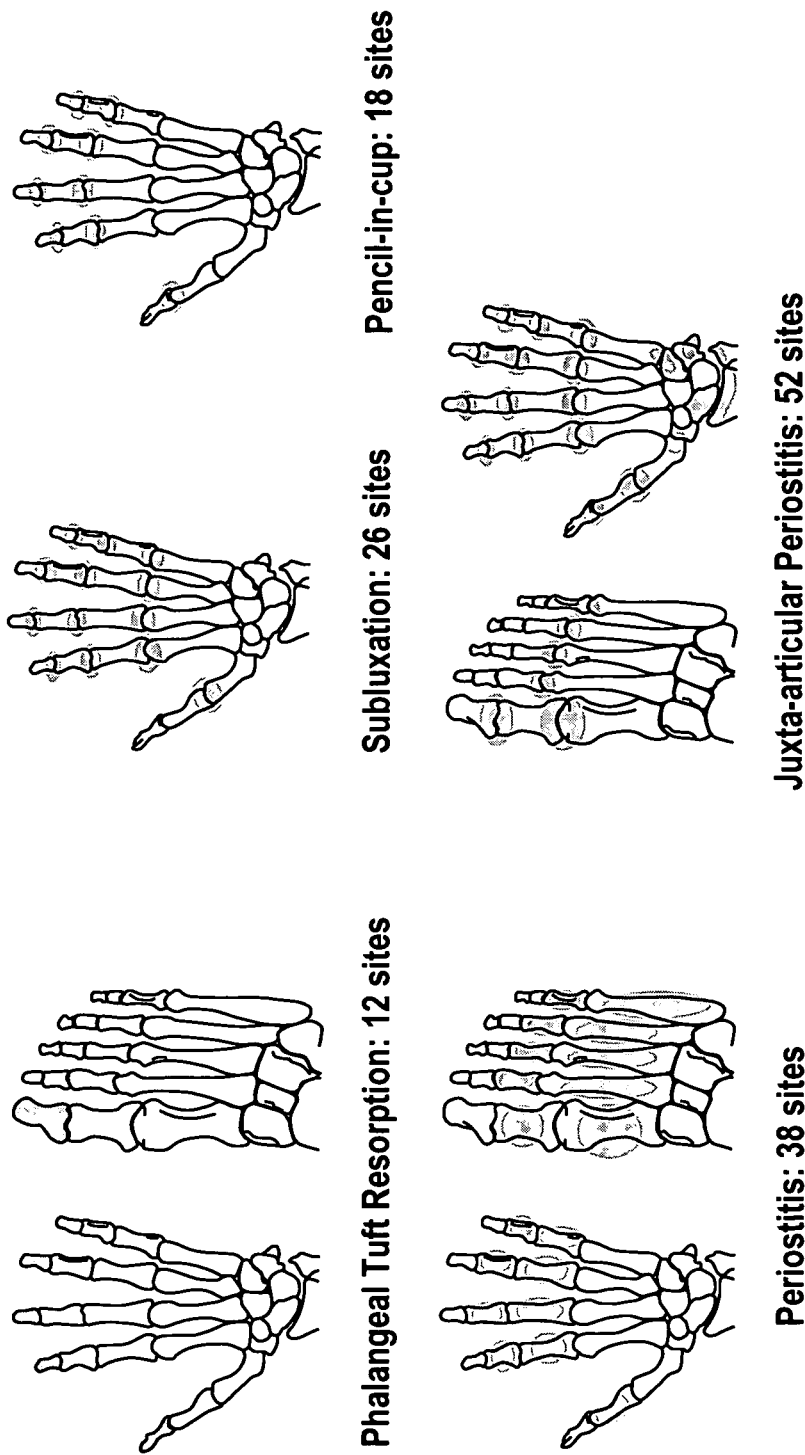

Radiographic assessments were performed during both the blinded portion (Weeks 0 and 24) and the open-label portion (Week 48). Radiographs of the hands and feet were assessed by a modified total Sharp score (mTSS) in which additional joints typically involved in PsA were added, and, to better quantify the significant osteolysis that occurs in PsA, the numerical scales were expanded. The mTSS was determined by combining the joint space narrowing score (0-192) and the erosion score (0-378), as shown in FIG. 1a. Clinical findings associated with PsA, e.g., pencil-in-cup changes, were also evaluated. Diagrams of the mTSS and the radiographic findings associated with PsA used in this study are shown in FIGS. 1a and 1b, respectively.

The radiograph reading procedure included the following. All films were read by two independent readers who were blinded to treatment and film order. Read number 1 was an evaluation of baseline and week 24 films. Read number 2 was an evaluation of baseline, week 24, and week 48 films.

Several sensitivity analyses were utilized to assess the impact of missing radiographs (imputation of zero change, worst rank change, $50^{th}/75^{th}$ percentile change based on patients with similar baseline scores, and linear extrapolation when multiple radiographs were available).

Week 24 analysis included the following: inclusion in the week 24 analysis required both baseline and week 24 films, where at least 50% of the joints were evaluable. Week 48 analysis included the following: All patients from the 24 week analysis were included in the week 48 analysis. If the week 48 film was not available (or <50% of the joints evaluable), then the following imputation was performed: if originally randomized to placebo, a change of 0 was imputed; and if originally randomized to adalimumab, linear extrapolation using first two films was conducted.

Baseline demographics and disease severity characteristics were consistent with moderate to severe PsA and were well-matched between treatment arms (adalimumab N=151, placebo N=162; mean±SD): age 49.0±11.8 yrs; duration of PsA 9.5±8.5 yrs; SJC (76) 14±12; TJC (78) 25±18; HAQ 1.0±0.6; mTSS 20.8±40.9; 51% were taking concomitant methotrexate. Of the total, 296 patients had X-rays at baseline and Week 24, and 265 patients also had X-rays at Week 48.

As reported in previous studies, the ACR20, 50, and 70 responses and the PASI 50, 75, and 90 responses for adalimumab-treated patients at week 24 were significantly better than placebo. ACR and PASI responses at week 24 are shown below in tables 1 and 2 (all results p≤0.001 placebo vs. adalimumab):

TABLE 1

ACR response: % of patients

|  | ACR20 | ACR50 | ACR70 |
| --- | --- | --- | --- |
| Placebo (N = 162) | 15 | 6 | 1 |
| Adalimumab (N = 151) | 57 | 39 | 23 |

TABLE 2

PASI response: % of patients

|  | PASI 50 | PASI 75 | PASI 90 |
| --- | --- | --- | --- |
| Placebo (N = 69) | 12 | 1 | 0 |
| Adalimumab (N = 69) | 75 | 59 | 42 |

Figure 2:
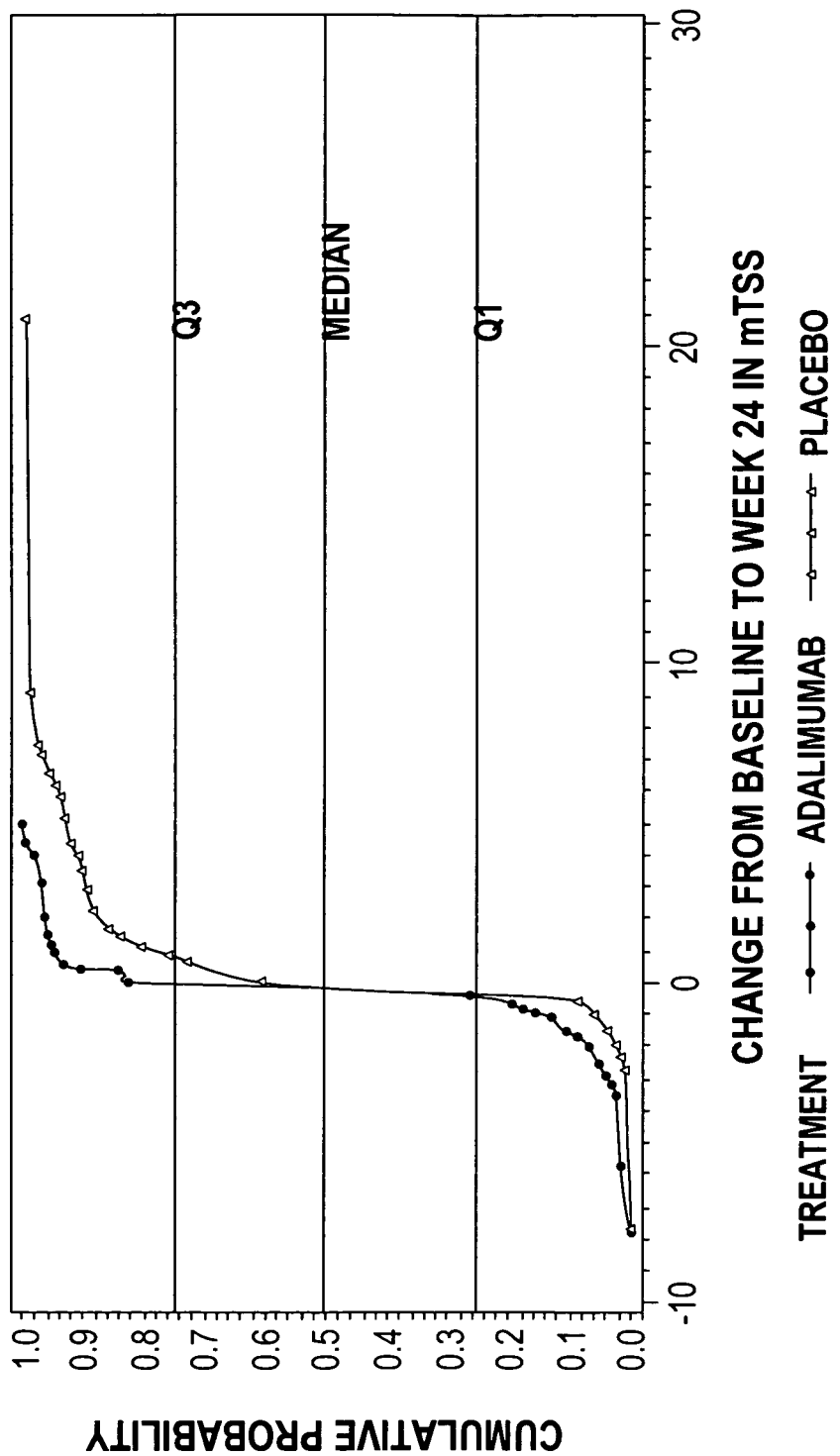
FIG. 2 shows a cumulative distribution function plot of modified Total Sharps Score (mTSS). The graph shows the change in baseline to Week 24 for subjects with both baseline and Week 24 radiographic films.

During the blinded study period (24 wks), adalimumab patients had significantly less progression in mTSS than placebo patients (mean change in mTSS −0.2 vs. 1.0, p<0.001, ranked ANCOVA). Statistical significance was maintained in all sensitivity analyses. FIG. 2 shows the distribution of mTSS scores which demonstrates that fewer patients treated with adalimumab had an increase in structural damage during 24 weeks of treatment compared with placebo. The difference in distribution was observed by looking at mean scores at week 24 and the number and percentage of patients who had an increase in Sharp score during the study (see Table 3). Approximately three times as many placebo-treated patients had an increase in mTSS (>0.5 units) than adalimumab-treated patients during the first 24 weeks of treatment.

TABLE 3

Change* in Modified Total Sharp Score at Week 24

|  | Placebo N = 152 n (%) | Adalimumab N = 144 n (%) |
| --- | --- | --- |
| Decrease in Sharp Score | 8 (5.3%) | 27 (18.8%) |
| No change in Sharp Score | 100 (65.8%) | 104 (72.2%) |
| Increase in Sharp Score | 44 (28.9%) | 13 (9.0%) | p ≤ 0.001 placebo vs. adalimumab using CMH test
*Change defined as >0.5 units in mTSS Score Statistically significant differences were observed between adalimumab and placebo treated subjects for both erosion scores and joint narrowing scores (p≤0.001 using a ranked ANACOVA). At Week 24, the change in erosion scores (change from baseline) were 0.6 for placebo patients and 0.0 for adalimumab patients (p<0.001, ranked ANCOVA), and the change in joint space narrowing scores (change from baseline) were 0.4 for placebo patients and −0.2 for adalimumab patients (p<0.001, ranked ANCOVA).

Sensitivity analyses to account for missing patients films were performed and results maintained statistical significance with all analyses. Post-hoc sensitivity analyses excluding feet and DIPs were as follows: one analysis was run excluding feet and DIPs and a second analysis was run excluding all DIP joints. Statistical significance was maintained in both analyses.

Figure 3:
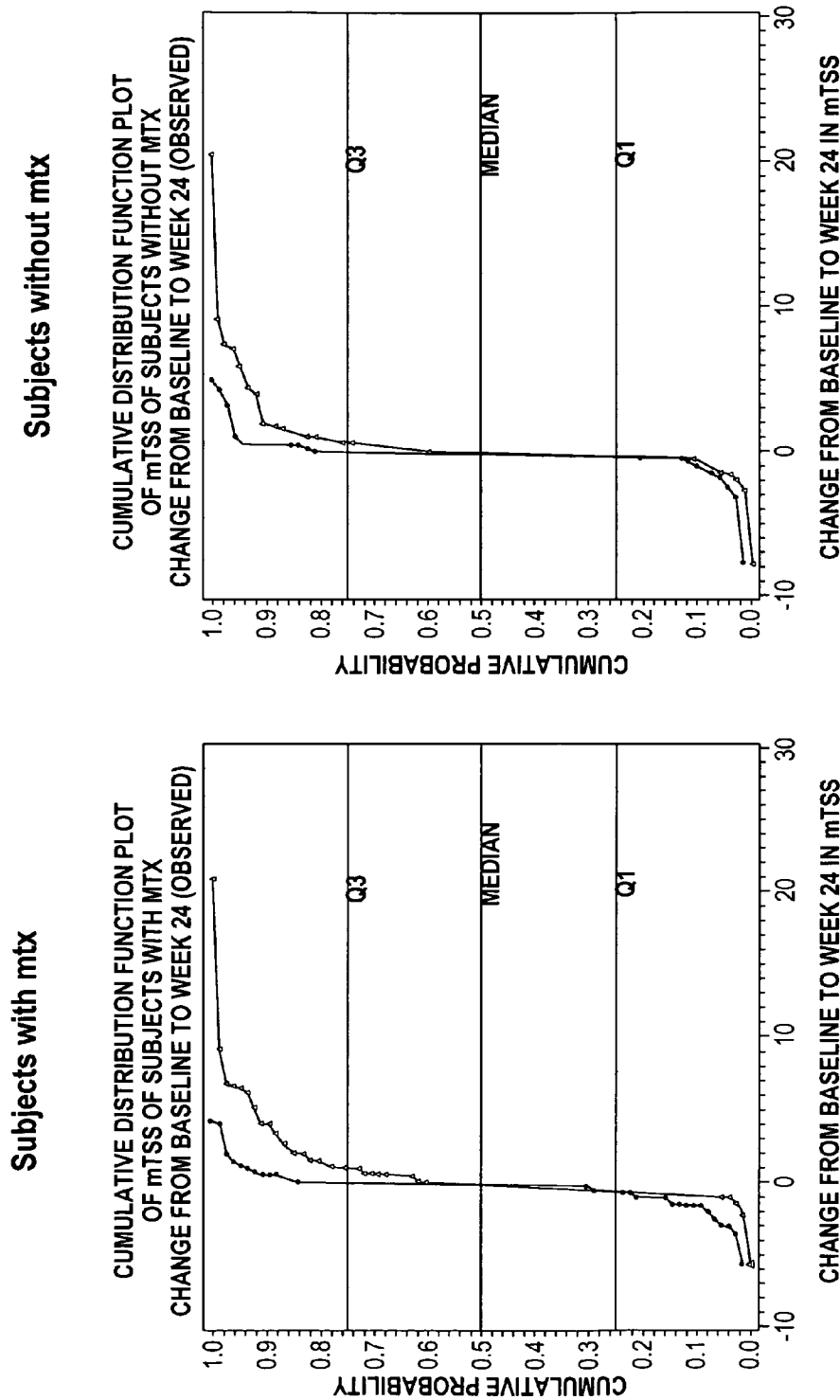
FIGS. 3a and 3b show cumulative distribution function plots of mTSS of subjects with (FIG. 3a) and without (FIG. 3b) methotrexate (mtx).

Statistically significant differences were observed between adalimumab and placebo treated subjects regardless of whether concomitant MTX was being used. Mean differences were slightly higher for patients taking concomitant MTX. Patients on monotherapy showed a change from baseline of −0.1 in adalimumab (n=68) vs. 0.9 for placebo (n=74) (p≤0.001 using a ranked ANACOVA). Patients on concomitant MTX showed a change from baseline of −0.3 in adalimumab (n=76) vs. 1.2 for placebo (n=78) (p≤0.001 using a ranked ANACOVA). FIGS. 3a and 3b show cumulative distribution function plots of mTSS of subjects with and without MTX.

Figure 4:
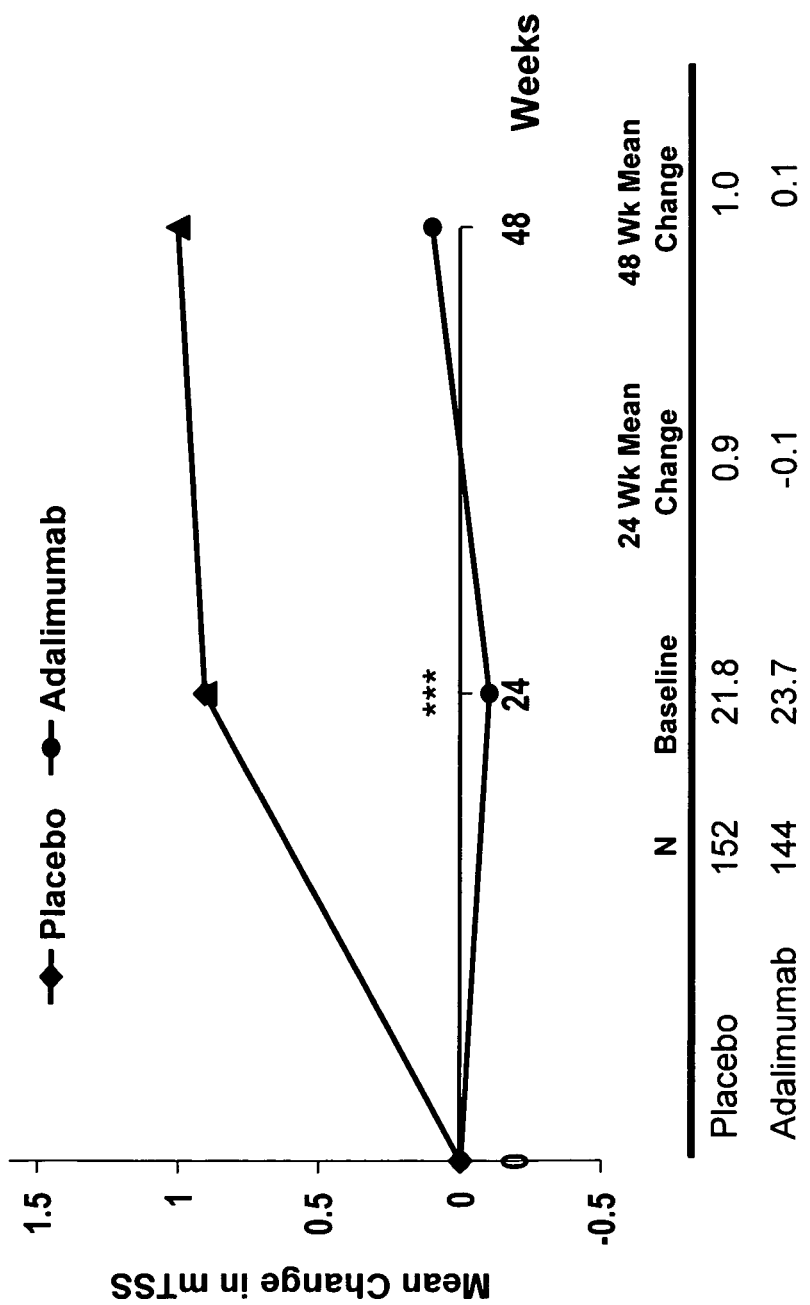
FIG. 4 shows a graph of the mean change in mTSS at Week 48.

Analysis of 48-week radiographs demonstrated that the lack of progression (lack of changes in mTSS) observed at Week 24 was maintained to Week 48 in adalimumab patients (see FIG. 4). Patients treated with placebo for 24 weeks did not have radiographic progression of disease during the open-label period. Neither treatment arm demonstrated significant progression in PsA-associated features. The prevalence of PsA-associated findings are shown in Table 4. No significant difference was found between groups at baseline, and no significant progression was found in either group during the 24-week study.

TABLE 4

Prevalence of PsA-associated findings

| | All patients (N = 313) n (%) |
|---|---|
| Joint space widening | 38 (12.1%) |
| Gross osteolysis | 60 (19.2%) |
| Subluxation | 49 (15.7%) |
| Pencil-in-cup | 9 (2.9%) |
| Juxta-articular periostitis | 247 (78.9%) |
| Shaft periostitis | 140 (44.7%) |
| Phalangeal tuft resorption | 224 (71.6%) |

Furthermore, adalimumab was generally well-tolerated as reported previously.

Adalimumab was more effective compared with placebo in inhibiting radiographic disease progression over a 24-week period. Adalimumab showed differences versus placebo both in patients taking concomitant methotrexate and in those taking adalimumab as monotherapy. The inhibition of structural damage progression observed in adalimumab-treated patients at 24 weeks was maintained at one year. In conclusion, this study demonstrated that adalimumab was effective in treating erosive polyarthritis and radiographic disease progression over one year in patients who also had moderate to severely active PsA.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference

What is claimed:

1. A method for inhibiting radiographic disease progression in a human subject having erosive polyarthritis associated with a disorder in which TNFα activity is detrimental, comprising administering to the subject having erosive polyarthritis an isolated human anti-TNFα antibody, or antigen-binding portion thereof, such that radiographic disease progression is inhibited in the subject, wherein a Total Sharp Score (TSS) of the subject is either maintained or decreased following administration of the human anti-TNFα antibody, or antigen-binding portion thereof, wherein the human anti-TNFα antibody, or an antigen-binding portion thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

2. The method of claim 1, wherein the human anti-TNFα antibody is golimumab, or an antigen-binding portion thereof.

3. The method of claim 1, wherein the human anti-TNFα antibody, or an antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2.

4. The method of claim 1, wherein the human anti-TNFα antibody is adalimumab, or an antigen-binding portion thereof.

5. The method of claim 1, wherein the human anti-TNFα antibody, or antigen-binding portion thereof, is administered to the subject on a biweekly dosing regimen.

6. The method of claim 1, further comprising administering an additional therapeutic agent to the subject.

7. The method of claim 6, wherein the additional therapeutic agent is methotrexate.

8. A method for treating erosive polyarthritis comprising administering to a subject having erosive polyarthritis associated with a disorder in which TNFα activity is detrimental, an amount of a isolated human anti-TNFα antibody, or an antigen-binding portion thereof, such that erosive polyarthritis is treated, wherein the amount of the human TNFα antibody, or antigen-binding portion thereof, results in a statistically significant reduction or inhibition in joint damage as measured by a Total Sharp Score (TSS), wherein the human anti-TNFα antibody, or an antigen-binding portion thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

9. The method of claim 8, wherein the disorder in which TNFα is detrimental is an autoimmune disease or a spondyloarthropathy.

10. The method of claim 9, wherein the autoimmune disorder is rheumatoid arthritis or juvenile rheumatoid arthritis.

11. The method of claim 9, wherein the spondyloarthropathy is ankylosing spondylitis or psoriatic arthritis.

12. The method of claim 8, further comprising administering an additional therapeutic agent to the subject.

13. The method of claim 8, wherein the additional therapeutic agent is methotrexate.

14. A method for inhibiting radiographic progression of joint disease associated with erosive polyarthritis in a subject having erosive polyarthritis associated with psoriatic arthritis or rheumatoid arthritis, said method comprising administering to the subject having erosive polyarthritis, adalimumab on a biweekly dosing regimen, such that radiographic progression is inhibited, wherein a Total Sharp Score (TSS) of the subject is maintained or decreased following administration of adalimumab.

15. The method of claim 1, wherein the disorder in which TNFα is detrimental is an autoimmune disease or a spondyloarthropathy.

16. The method of claim 15, wherein the autoimmune disease is rheumatoid arthritis or juvenile rheumatoid arthritis.

17. The method of claim 15, wherein the spondyloarthropathy is ankylosing spondylitis or psoriatic arthritis.

18. The method of claim 8, wherein the human anti-TNFα antibody, or an antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2.

19. The method of claim 8, wherein the human anti-TNFα antibody is adalimumab, or an antigen-binding portion thereof.

20. The method of claim 8, wherein the human anti-TNFα antibody, or antigen-binding portion thereof, is administered to the subject on a biweekly dosing regimen.

21. The method of claim 8, wherein the human anti-TNFα antibody, or antigen-binding portion thereof, is administered at a dose of about 40 mg.

22. A method for treating erosive polyarthritis associated with a disorder in which TNFα activity is detrimental, said method comprising identifying a subject having erosive polyarthritis associated with a disorder in which TNFα activity is detrimental and administering to the subject an amount of an isolated human anti-TNFα antibody, or an antigen-binding portion thereof, such that erosive polyarthritis is treated, wherein the human anti-TNFα antibody, or an antigen-binding portion thereof, dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

23. The method of claim 22, wherein the human anti-TNFα antibody is golimumab, or an antigen-binding portion thereof.

24. The method of claim 22, wherein the human anti-TNFα antibody, or an antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2.

25. The method of claim 22, wherein the human anti-TNFα antibody is adalimumab, or an antigen-binding portion thereof.

26. The method of claim 22, wherein the human anti-TNFα antibody, or antigen-binding portion thereof, is administered to the subject on a biweekly dosing regimen.

27. The method of claim 22, wherein the disorder is rheumatoid arthritis, or juvenile rheumatoid arthritis.

28. The method of claim 22, further comprising administering an additional therapeutic agent to the subject.

29. The method of claim 28, wherein the additional therapeutic agent is methotrexate.

30. The method of claim 1, wherein the human anti-TNFα antibody, or antigen-binding portion thereof, comprises:
a light chain variable region (LCVR) comprising a CDR3 domain set forth in the amino acid sequence of SEQ ID NO: 3, or modified from SEQ ID NO: 3 by a single alanine substitution at position 1, 4, 5, 7, and/or 8 or by one to five conservative amino acid substitutions at positions 1, 3, 4, 6, 7, 8 and/or 9, a CDR2 domain set forth in the amino acid sequence of SEQ ID NO: 5, and a CDR1 domain set forth in the amino acid sequence of SEQ ID NO: 7;
and a heavy chain variable region (HCVR) comprising a CDR3 domain set forth in the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12, a CDR2 domain set forth in the amino acid sequence of SEQ ID NO: 6, and a CDR1 domain set forth in the amino acid sequence of SEQ ID NO: 8.

31. The method of claim 8, wherein the human anti-TNFα antibody, or antigen-binding portion thereof, comprises:
   a light chain variable region (LCVR) comprising a CDR3 domain set forth in the amino acid sequence of SEQ ID NO: 3, or modified from SEQ ID NO: 3 by a single alanine substitution at position 1, 4, 5, 7, and/or 8 or by one to five conservative amino acid substitutions at positions 1, 3, 4, 6, 7, 8 and/or 9, a CDR2 domain set forth in the amino acid sequence of SEQ ID NO: 5, and a CDR1 domain set forth in the amino acid sequence of SEQ ID NO: 7; and
   a heavy chain variable region (HCVR) comprising a CDR3 domain set forth in the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12, a CDR2 domain set forth in the amino acid sequence of SEQ ID NO: 6, and a CDR1 domain set forth in the amino acid sequence of SEQ ID NO: 8.

32. The method of claim 14, wherein the human anti-TNFα antibody, or antigen-binding portion thereof, comprises:
   a light chain variable region (LCVR) comprising a CDR3 domain set forth in the amino acid sequence of SEQ ID NO: 3, or modified from SEQ ID NO: 3 by a single alanine substitution at position 1, 4, 5, 7, and/or 8 or by one to five conservative amino acid substitutions at positions 1, 3, 4, 6, 7, 8 and/or 9, a CDR2 domain set forth in the amino acid sequence of SEQ ID NO: 5, and a CDR1 domain set forth in the amino acid sequence of SEQ ID NO: 7; and
   a heavy chain variable region (HCVR) comprising a CDR3 domain set forth in the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12, a CDR2 domain set forth in the amino acid sequence of SEQ ID NO: 6, and a CDR1 domain set forth in the amino acid sequence of SEQ ID NO: 8.

33. The method of claim 22, wherein the human anti-TNFα antibody, or antigen-binding portion thereof, comprises:
   a light chain variable region (LCVR) comprising a CDR3 domain set forth in the amino acid sequence of SEQ ID NO: 3, or modified from SEQ ID NO: 3 by a single alanine substitution at position 1, 4, 5, 7, and/or 8 or by one to five conservative amino acid substitutions at positions 1, 3, 4, 6, 7, 8 and/or 9, a CDR2 domain set forth in the amino acid sequence of SEQ ID NO: 5, and a CDR1 domain set forth in the amino acid sequence of SEQ ID NO: 7; and
   a heavy chain variable region (HCVR) comprising a CDR3 domain set forth in the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12, a CDR2 domain set forth in the amino acid sequence of SEQ ID NO: 6, and a CDR1 domain set forth in the amino acid sequence of SEQ ID NO: 8.

\* \* \* \* \*

SEQUENCE LISTING

```
<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: D2E7 light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
```

```
<220> FEATURE:
<223> OTHER INFORMATION: D2E7 heavy chain variable region

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: D2E7 light chain variable region CDR3
<220> FEATURE:
<221> NAME/KEY: VARIANT
<222> LOCATION: )9
<223> OTHER INFORMATION: Xaa = Any Amino Acid

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: D2E7 heavy chain variable region CDR3
<220> FEATURE:
<221> NAME/KEY: VARIANT
<222> LOCATION: 12
<223> OTHER INFORMATION: Xaa = Any Amino Acid

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: D2E7 light chain variable region CDR2

<400> SEQUENCE: 5

Ala Ala Ser Thr Leu Gln Ser
1               5

<210> SEQ ID NO 6
<211> LENGTH: 17
<212> TYPE: PRT
```

```
<213> ORGANISM: Artificial Sequence
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
 1               5                  10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial Sequence
<220> FEATURE:
<223> OTHER INFORMATION: D2E7 heavy chain variable region CDR1

<400> SEQUENCE: 8

Asp Tyr Ala Met His
 1               5

<210> SEQ ID NO 9
<211> LENGTH: 107
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
 1               5                  10                  15
```

```
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
            35                  40                  45

Ser Ala Ile Thr Trp Asn Ser Gly His Ile Asp Tyr Ala Asp Ser Val
        50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

Gln Lys Tyr Asn Ser Ala Pro Tyr Ala
1               5

<210> SEQ ID NO 12
<211> LENGTH: 9
<212> TYPE: PRT
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
1               5

<210> SEQ ID NO 15
<211> LENGTH: 9
<212> TYPE: PRT
<213> ORGANISM: Artificial Sequence
<220> FEATURE:
```

```
<223> OTHER INFORMATION: VLL100D2 light chain variable region CDR3

<400> SEQUENCE: 15

Gln Lys Tyr Asn Ser Ala Pro Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
1               5

<210> SEQ ID NO 17
<211> LENGTH: 9
<212> TYPE: PRT
<213> ORGANISM: Artificial Sequence
<220> FEATURE:
<223> OTHER INFORMATION: L0E5 light chain variable region CDR3

<400> SEQUENCE: 17

Gln Lys Tyr Asn Ser Ala Pro Tyr Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: VLLOG7 light chain variable region CDR3

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial Sequence
<220> FEATURE:
<223> OTHER INFORMATION: VLLOG9 light chain variable region CDR3

<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: VLLOH1 light chain variable region CDR3

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial Sequence
<220> FEATURE:
<223> OTHER INFORMATION: VLLOH10 light chain variable region CDR3
```

```
<400> SEQUENCE: 21

Gln Lys Tyr Asn Ser Ala Ala Tyr Ser
 1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr
 1               5

<210> SEQ ID NO 23
<211> LENGTH: 9
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
 1               5

<210> SEQ ID NO 24
<211> LENGTH: 9
<212> TYPE: PRT
<213> ORGANISM: Artificial Sequence
<220> FEATURE:
<223> OTHER INFORMATION: VL0.1F4 light chain variable region CDR3

<400> SEQUENCE: 24

Gln Lys Tyr Ile Ser Ala Pro Tyr Thr
 1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
 1               5

<210> SEQ ID NO 26
<211> LENGTH: 9
<212> TYPE: PRT
<213> ORGANISM: Artificial Sequence
<220> FEATURE:
<223> OTHER INFORMATION: L0E7.A light chain variable region CDR3

<400> SEQUENCE: 26

Gln Arg Tyr Asn Arg Ala Pro Tyr Ala
 1               5

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27
```

```
Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10
```

```
<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
 1               5                  10

<210> SEQ ID NO 36
<211> LENGTH: 321
<212> TYPE: DNA
<213> ORGANISM: Artificial Sequence
<220> FEATURE:
<223> OTHER INFORMATION: D2E7 light chain variable region

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321

<210> SEQ ID NO 37
<211> LENGTH: 363
<212> TYPE: DNA
<213> ORGANISM: Artificial Sequence
<220> FEATURE:
<223> OTHER INFORMATION: D2E7 heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tggagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                   363
```